(12) United States Patent
Lotz et al.

(10) Patent No.: US 7,375,241 B2
(45) Date of Patent: May 20, 2008

(54) FERROCENYL-1,2-DIPHOSPHINES, THE PRODUCTION THEREOF AND THEIR USE

(75) Inventors: Matthias Lotz, Basel (CH); Martin Kesselgruber, Basel (CH); Marc Thommen, Nuglar (CH); Benoît Pugin, Münchenstein (CH)

(73) Assignee: Solvias A.G., Basel (CH)

( * ) Notice: Subject to any disclaimer, the term of this patent is extended or adjusted under 35 U.S.C. 154(b) by 0 days.

(21) Appl. No.: 10/582,406

(22) PCT Filed: Dec. 10, 2004

(86) PCT No.: PCT/EP2004/053389

§ 371 (c)(1),
(2), (4) Date: Jun. 9, 2006

(87) PCT Pub. No.: WO2005/056568

PCT Pub. Date: Jun. 23, 2005

(65) Prior Publication Data

US 2007/0142655 A1    Jun. 21, 2007

(30) Foreign Application Priority Data

Dec. 12, 2003   (CH) .................................... 2131/03

(51) Int. Cl.
*C07F 5/02* (2006.01)
*C07F 15/00* (2006.01)
*C07C 229/00* (2006.01)
*C07C 69/34* (2006.01)

(52) U.S. Cl. ............................ 556/8; 556/14; 556/18; 560/155; 560/170; 560/190

(58) Field of Classification Search .................. 556/14, 556/18, 8; 560/155, 170, 190
See application file for complete search history.

(56) References Cited

U.S. PATENT DOCUMENTS

| | | | |
|---|---|---|---|
| 5,986,139 A | 11/1999 | Sablong et al. | ............. 564/415 |
| 6,008,393 A * | 12/1999 | Sablong et al. | ............... 556/18 |
| 6,169,192 B1 * | 1/2001 | Pugin et al. | .................... 556/11 |
| 6,191,284 B1 * | 2/2001 | Knochel et al. | ............. 548/402 |
| 6,218,559 B1 * | 4/2001 | Spindler et al. | ............... 556/14 |
| 6,777,567 B2 * | 8/2004 | Weissensteiner et al. | ...... 556/16 |
| 7,009,065 B2 * | 3/2006 | Knochel et al. | ............. 556/14 |
| 7,015,342 B2 * | 3/2006 | Knochel et al. | ............. 556/14 |

FOREIGN PATENT DOCUMENTS

WO    97/05094    2/1997

OTHER PUBLICATIONS

Tania Ireland et al., "Ferrocenylliganden mit zwei Phosphanyl-substituenten in α,ε-Position für die Übergangsmetall-katalysierte asymmetrische Hydrierung funktionalisierter Doppelbindungen", Angewandte Chem., VCH, Verlagsgesellschaft, Weinheim, DE, vol. 111, No. 21, 1999, pp. 3397-3400, XP002179596, ISSN: 0044-8249.

* cited by examiner

*Primary Examiner*—Porfirio Nazario-Gonzalez
(74) *Attorney, Agent, or Firm*—Wenderoth, Lind & Ponack, L.L.P.

(57) ABSTRACT

The invention relates to compounds of formula (I) provided in the form of racemic compounds, mixtures of diastereomers or essentially pure diastereomers, wherein $R_1$ represents a hydrogen atom or $C_1$-$C_4$-alkyl, and at least one secondary phosphine depicts an unsubstituted or substituted cyclic phosphine group, or phosphonium salts thereof having one or two monovalent anions or a divalent anion. The compounds of formula (I) can be obtained by means of a novel method and are valuable ligands for catalytically active metal complexes in asymmetrical synthesis

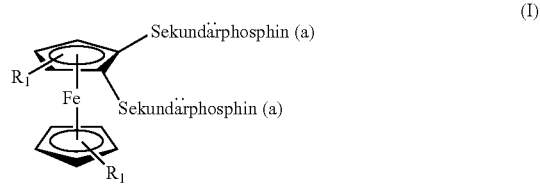

(a) SECONDARY PHOSPHINE.

14 Claims, No Drawings

FERROCENYL-1,2-DIPHOSPHINES, THE PRODUCTION THEREOF AND THEIR USE

The present invention relates to 1,2-di-sec-phosphinoferrocenes having at least one cyclic phosphine group, a process for preparing them; metal complexes comprising these diphosphinoferrocenes; and the use of the metal complexes as catalysts for enantioselective addition reactions with prochiral organic compounds.

Chiral diphosphines are useful ligands for asymmetric catalysis, in particular for the enantioselective hydrogenation of unsaturated, prochiral, organic compounds. Recently, diphosphines having cyclic sec-phosphino radicals (for example phosphetane or phospholane radicals) have also become known for this purpose. Thus, EP-B1-0 592 552 and M. J. Burk in Acc. of Chem. Res. Vol. 33, No. 6 (2000), pages 363 to 372, describe 1,2-diphospholanes derived from, for example, benzene or ethane and also 1,1'-ferrocenyldiphospholanes, their preparation via cyclic butanediol sulfates and their use in metal complexes for enantioselective catalysis. The phospholane radicals are substituted in the α,α' positions by, for example, methyl or ethyl in order to achieve the desired chirality. In the case of the 1,1'-ferrocenyldiphospholanes, the phospholane groups are each bound to one of the two cyclopentadienyl rings. U. Berens et al. in Angew. Chem. 112 (11) pages 2057-2060 (2000) describe 1,1'-diphosphetanylferrocenes having α,α' substituents such as methyl. 1,1'-Diphosphetanylferrocenes are also mentioned in WO 98/02445. Benzene-1,2-diphospholanes whose phospholane rings are additionally substituted by alkoxy groups are proposed in EP-B1-0 889 048.

The best method of preparing cyclic secondary phosphines has hitherto proven to be the reaction of primary diphosphines with substituted or unsubstituted alkylene sulfates (cf. M. J. Burk in J. Am. Chem. Soc. 1991, 113, pages 8518-8519). The preparation of primary diphosphines has not yet been described at all in the ferrocene series, for example ferrocene-1,2-diphosphines. Ferrocenyl-1,2-di-sec-phosphines having at least one cyclic phosphine group are not yet known because of the synthetic difficulties.

It has now surprisingly been found that the unactivated hydrogen atom in the ortho position relative to the phosphine group in ferrocene-monophosphines can be metalated regioselectively in high yields by means of organic lithium or magnesium compounds when the phosphine group contain s amino and/or oxy substituents. The reaction proceeds particularly well when borane of the formula $BH_3$ is additionally bound to the P atom. These metalated ferrocene-monophosphines can be converted in a simple manner, in surprisingly high yields and even on an industrial scale, into ferrocene-1,2-di-sec-phosphines having at least one cyclic sec-phosphino group.

In ferrocenes, planar chirality is generated on metalation. Surprisingly, it has also been found that metalation proceeds highly stereoselectively when the N or O atoms in the phosphine group of the monophosphinoferrocenes bear chiral radicals which, in particular, have a chiral carbon atom in the α or β position relative to the N or O atoms. In this way, the synthesis directly gives diastereomers in high optical yields, so that complicated separation operations are avoidable. Metal complexes comprising the ferrocene-1,2-di-sec-phosphines are highly suitable for asymmetric hydrogenation in high chemical and optical yields.

The invention firstly provides compounds of the formula I in the form of racemates, mixtures of diastereomers or essentially pure diastereomers,

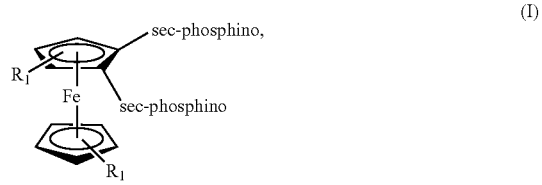

where
$R_1$ is a hydrogen atom or $C_1$-$C_4$-alkyl and at least one sec-phosphino group is an unsubstituted or substituted cyclic phosphino group.

An alkyl radical $R_1$ can be, for example, methyl, ethyl, n- or i-propyl, n-, i- or t-butyl. $R_1$ is preferably a hydrogen atom.

The acyclic, secondary phosphino group can bear two identical or two different hydrocarbon radicals. The phosphino group preferably bears two identical hydrocarbon radicals. The hydrocarbon radicals can be unsubstituted or substituted and can have from 1 to 22, preferably from 1 to 12 and particularly preferably from 1 to 8, carbon atoms. A preferred acyclic sec-phosphino group is one in which the phosphino group bears two identical or different radicals selected from the group consisting of linear or branched $C_1$-$C_{12}$-alkyl; unsubstituted or $C_1$-$C_6$-alkyl- or $C_1$-$C_6$-alkoxy-substituted $C_5$-$C_{12}$-cycloalkyl or $C_5$-$C_{12}$-cycloalkyl-$CH_2$—; phenyl or benzyl; phenyl or benzyl substituted by halogen (for example F, Cl or Br), $C_1$-$C_6$-alkyl, $C_1$-$C_6$-haloalkyl (for example trifluoromethyl), $C_1$-$C_6$-alkoxy, $C_1$-$C_6$-haloalkoxy (for example trifluoromethoxy), $(C_6H_5)_3$Si, $(C_1$-$C_{12}$-alkyl)$_3$Si, sec-amino or —$CO_2$—$C_1$-$C_6$-alkyl (for example —$CO_2CH_3$).

Examples of alkyl substituents on P, which preferably have from 1 to 6 carbon atoms, are methyl, ethyl, n-propyl, i-propyl, n-butyl, i-butyl, t-butyl and the isomers of pentyl and hexyl. Examples of unsubstituted or alkyl-substituted cycloalkyl substituents on P are cyclopentyl, cyclohexyl, methylcyclohexyl and ethylcyclohexyl and dimethylcyclohexyl. Examples of alkyl-, alkoxy-, haloalkyl- and haloalkyl-substituted phenyl and benzyl substituents on P are methylphenyl, dimethylphenyl, trimethylphenyl, ethylphenyl, methylbenzyl, methoxyphenyl, dimethoxyphenyl, trifluoromethylphenyl, bistrifluoromethylphenyl, tristrifluoromethylphenyl, trifluoromethoxyphenyl, bistrifluoromethoxyphenyl and 3,5-dimethyl4-methoxyphenyl.

Preferred phosphino groups are ones which bear identical or different and preferably identical radicals selected from the group consisting of $C_1$-$C_6$-alkyl, unsubstituted cyclopentyl or cyclohexyl and cyclopentyl or cyclohexyl substituted by from 1 to 3 $C_1$-$C_4$-alkyl or $C_1$-$C_4$-alkoxy groups, benzyl and in particular phenyl which are unsubstituted or substituted by from 1 to 3 $C_1$-$C_4$-alkyl, $C_1$-$C_4$-alkoxy, F, Cl, $C_1$-$C_4$-fluoroalkyl or $C_1$-$C_4$-fluoroalkoxy substituents.

The sec-phosphino group preferably corresponds to the formula —$PR_2R_3$, where $R_2$ and $R_3$ are each, independently of one another, a hydrocarbon radical which has from 1 to 20 carbon atoms and may be unsubstituted or substituted by halogen, $C_1$-$C_6$-alkyl, $C_1$-$C_6$-haloalkyl, $C_1$-$C_6$-alkoxy, $C_1$-$C_6$-haloalkoxy, di-$C_1$-$C_4$-alkylamino, $(C_6H_5)_3$Si, $(C_1$-$C_{12}$-alkyl)$_3$Si or —$CO_2$—$C_1$-$C_6$-alkyl.

$R_2$ and $R_3$ are preferably identical or different and in particular identical radicals selected from the group consisting of linear or branched $C_1$-$C_6$-alkyl, unsubstituted cyclopentyl or cyclohexyl and cyclopentyl or cyclohexyl substituted by from one to three $C_1$-$C_4$-alkyl or $C_1$-$C_4$-alkoxy groups, unsubstituted benzyl or benzyl substituted by from one to three $C_1$-$C_4$-alkyl or $C_1$-$C_4$-alkoxy groups and in particular unsubstituted phenyl or phenyl substituted by from one to three $C_1$-$C_4$-alkyl, $C_1$-$C_4$-alkoxy, —$NH_2$, OH, F, Cl, $C_1$-$C_4$-fluoroalkyl or $C_1$-$C_4$-fluoroalkoxy.

$R_2$ and $R_3$ are particularly preferably identical or different and in particular identical radicals selected from the group consisting of $C_1$-$C_6$-alkyl, cyclopentyl, cyclohexyl and unsubstituted phenyl or phenyl substituted by from one to three $C_1$-$C_4$-alkyl, $C_1$-$C_4$-alkoxy and/or $C_1$-$C_4$-fluoroalkyl groups.

Cyclic sec-phosphino can correspond to the formula II, IIa, IIb or IIc,

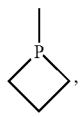

(II)

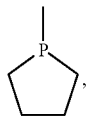

(IIa)

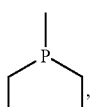

(IIb)

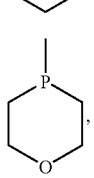

(IIc)

which are unsubstituted or substituted by one or more —OH, $C_1$-$C_8$-alkyl, $C_1$-$C_8$-hydroxyalkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkyl- or $C_1$-$C_4$-alkoxyphenyl, benzyl, $C_1$-$C_4$-alkyl- or $C_1$-$C_4$-alkoxybenzyl, benzyloxy, $C_1$-$C_4$-alkyl- or $C_1$-$C_4$-alkoxybenzyloxy or $C_1$-$C_4$-alkylidenedioxyl groups.

The substituents can be present in one or both α positions relative to the P atom in order to introduce chiral α-carbon atoms. Substituents in one or both α positions are preferably $C_1$-$C_4$-alkyl, $C_1$-$C_4$-hydroxyalkyl or benzyl, for example methyl, ethyl, n- or i-propyl, n-, i- or t-butyl, hydroxymethyl, 1- or 2-hydroxyethyl, 1-, 2- or 3-hydroxypropyl, benzyl or —$CH_2$—O—$C_1$-$C_4$-alkyl or —$CH_2$—O—$C_6$-$C_{10}$-aryl.

Substituents in the β,γ positions can be, for example, $C_1$-$C_4$-alkyl, $C_1$-$C_4$-hydroxyalkyl, $C_1$-$C_4$-alkoxy, benzyloxy or —O—$CH_2$—O—, —O—CH($C_1$-$C_4$-alkyl)-O— or —O—C($C_1$-$C_4$-alkyl)$_2$-O—. Some examples are methyl, ethyl, methoxy, ethoxy, —O—CH(methyl)-O— and —O—C(methyl)$_2$-O—.

Depending on the type of substitution and the number of substituents, the cyclic phosphino radicals can be C-chiral, P-chiral or a C- and P-chiral.

An aliphatic 5- or 6-ring or benzene can be fused onto two adjacent carbon atoms in the radicals of the formulae II to IIc.

The cyclic sec-phosphino group preferably corresponds to the formulae (only one of the possible diastereomers is indicated)

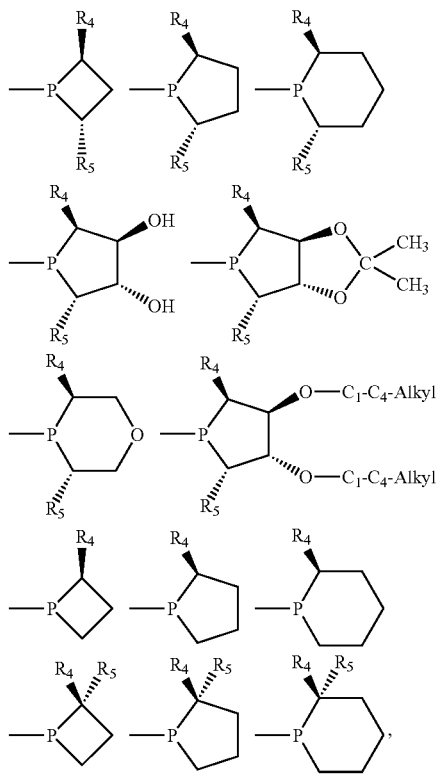

where the radicals $R_4$ and $R_5$ are each $C_1$-$C_4$-alkyl, $C_1$-$C_4$-hydroxyalkyl, for example methyl, ethyl, n- or i-propyl, hydroxymethyl, 1- or 2-hydroxyethyl, benzyl or —$CH_2$—O—$C_1$-$C_4$-alkyl or —$CH_2$—O—$C_6$-$C_{10}$-aryl and $R_4$ and $R_5$ are identical or different.

In a preferred embodiment, the compounds of the formula I correspond to the formula III or IV,

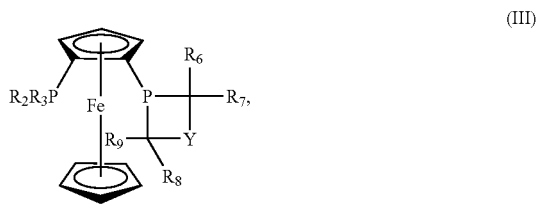

(III)

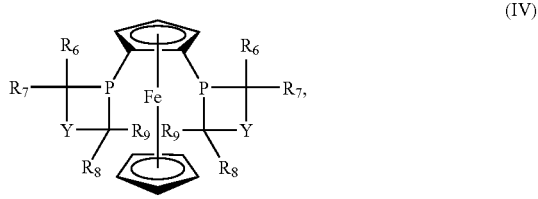

(IV)

where $R_2$ and $R_3$ have the abovementioned meanings, including the preferences, Y is —CH$_2$—, —CH$_2$CH$_2$—, —CH$_2$CH$_2$CH$_2$—, —CH(OH)CH(OH)—, —CH(OC$_1$-C$_4$-alkyl)CH(OC$_1$-C$_4$-alkyl)- or a radical of the formula

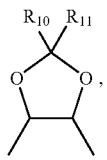

R$_6$, R$_7$, R$_8$ and R$_9$ are each, independently of one another, H, C$_1$-C$_4$-alkyl, C$_1$-C$_4$-hydroxyalkyl, benzyl or —CH$_2$—O—C$_1$-C$_4$-alkyl or —CH$_2$—O—C$_6$-C$_{10}$-aryl and at least one of the radicals R$_6$, R$_7$, R$_8$ and R$_9$ is C$_1$-C$_4$-alkyl or benzyl, R$_{10}$ is H or C$_1$-C$_4$-alkyl and R$_{11}$ is C$_1$-C$_4$-alkyl.

Preferred embodiments of the compounds of the formulae III and IV are ones in which R$_6$ is H, C$_1$-C$_4$-alkyl, C$_1$-C$_4$-hydroxyalkyl, benzyl or —CH$_2$—O—C$_1$-C$_4$-alkyl or —CH$_2$—O—C$_6$-C$_{10}$-aryl and R$_7$, R$_8$ and R$_9$ are each H, or R$_6$ and R$_8$ are each C$_1$-C$_4$-alkyl, C$_1$-C$_4$-hydroxyalkyl, benzyl or —CH$_2$—O—C$_1$-C$_4$-alkyl or —CH$_2$—O—C$_6$-C$_{10}$-aryl and R$_7$ and R$_9$ are each H, or R$_6$ and R$_7$ are each C$_1$-C$_4$-alkyl, C$_1$-C$_4$-hydroxyalkyl, benzyl or —CH$_2$—O—C$_1$-C$_4$-alkyl or —CH$_2$—O—C$_6$-C$_{10}$-aryl and R$_8$ and R$_9$ are each H. Alkyl is preferably methyl, ethyl, n- or i-propyl.

The novel compounds of the formula I are ligands for the formation of metal complexes. It can be advantageous with regard to stability and handling in air, to convert the compounds into phosphonium salts having one or two monovalent anions or one divalent anion. Complex formation is not adversely affected by this. If ligands of the formula I are present in solution, it can be advantageous for storage and transport to form salts in situ and not to isolate salts. However, salt formation can also be carried out directly before use, i.e. formation of metal complexes. Salt formation in solution can, for example, be effected using mineral acids such as hydrohalic acids or sulfuric acid, preferably HCl or HBr. It is also possible to use halocarboxylic acids, halosulfonic acids or complex acids which are more advantageous for the formation of crystalline and stable, isolatable salts. Examples of anions of such acids are R$_a$COO$^-$, R$_a$SO$_3^-$, BF$_4^-$, PF$_6^-$, AsF$_6^-$, SbF$_6^-$, B(C$_6$F$_5$)$_4^-$ or B(3,5-bis-trifluoromethylphenyl)$_4^-$, where R$_a$ is C$_1$-C$_6$-haloalkyl, C$_5$-C$_{10}$-halocycloalkyl or C$_6$-C$_{10}$-haloaryl.

The haloalkyl (for example C$_1$-C$_4$-haloalkyl), halocycloalkyl (for example C$_5$-C$_6$-halocycloalkyl) and haloaryl (for example halophenyl) can contain one or more halogen atoms and can be a perhalogenated radical. Halogen is preferably Cl and very particularly preferably F. Particular preference is given to perfluorinated radicals. Some examples are monochloromethyl, dichloromethyl and trichloromethyl, 1,1,1-trichloroethyl, 2,2-dichloroethyl, 1,2,2-trichloroethyl, pentachloroethyl, monofluoromethyl, difluoromethyl and trifluoromethyl, 2,2-difluoroethyl, 1,1,1-trifluoroethyl, 1,2,2-trifluoroethyl, pentafluoroethyl and pentafluorophenyl.

R$_a$ is particularly preferably C$_1$-C$_4$-perfluoroalkyl. Particularly preferred anions are CF$_3$COO$^-$, CF$_3$SO$_3^-$, BF$_4^-$, PF$_6^-$, AsF$_6^-$ and SbF$_6^-$.

The ferrocene-diphosphines of the invention can be prepared by means of a novel process in which a selective ortho-metalation of ferrocenylmonophosphines having P—O— and/or P—N— bonded and chiral or achiral radicals represents the key step in the reaction sequence. The process is modular for the creation of different substitution patterns on the two P atoms and gives high yields. In addition, pure diastereomers or pairs of easily separated pairs of diastereomers can be produced directly in a simple manner and high yields. The process is particularly useful for preparing the diphosphines of the invention on an industrial scale.

The invention further provides a process for preparing compounds of the formula I in the form of racemates, mixtures of diastereomers or essentially pure diastereomers,

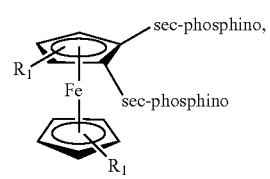

where

R$_1$ is a hydrogen atom or C$_1$-C$_4$-alkyl and at least one sec-phosphino is an unsubstituted or substituted cyclic phosphino group, which comprises the steps a) reaction of a compound of the formula V

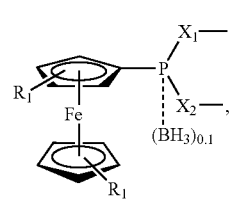

where

X$_1$ and X$_2$ are each, independently of one another, O or N and C-bonded hydrocarbon or heterohydrocarbon radicals are bound to the free bonds of the O and N atoms, with at least equivalent amounts of a lithium alkyl, a magnesium Grignard compound or an aliphatic Li sec-amide or X$_3$Mg sec-amide to form a compound of the formula VI,

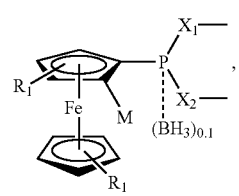

where

M is —Li or —MgX$_3$ and X$_3$ is Cl, Br or I, b) reaction of the compound of the formula VI with at least equivalent amounts of a di-sec-aminophosphine halide, a dialkoxyphosphine halide, di-sec-amino-P(O) halide, dialkoxy-P(O) halide or PCl$_3$ or PBr$_3$ to form a compound of the formula VII

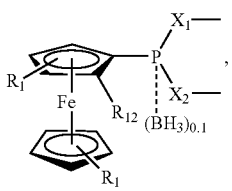
(VII)

where
$R_{12}$ is —$PCl_2$, —$PBr_2$, di(sec-amino)P—, dialkoxyP—, di-sec-amino-P(O)—, dialkoxy-P(O)—, and b1) removing any borane group present from a compound of the formula VII, then splitting off the radicals (hetero)hydrocarbon-$X_1$, (hetero)hydrocarbon-$X_2$ or $X_1$-(hetero)hydrocarbon-$X_2$ or di-sec-amino or dialkoxy by means of HCl or HBr to form a —$PCl_2$ group or —$PBr_2$ group and then hydrogenating the —(O)$PCl_2$ groups, —(O)$PBr_2$ groups, —$PCl_2$ groups or —$PBr_2$ groups to form a compound of the formula VIII or b2) splitting off the radicals (hetero)hydrocarbon-$X_1$, (hetero)hydrocarbon-$X_2$ or $X_1$-(hetero)hydrocarbon-$X_2$ or di-sec-amino or dialkoxy from a compound of the formula VII by means of HCl or HBr to form a —$PCl_2$ group or —$PBr_2$ group and then hydrogenating the —(O)$PCl_2$ groups, —(O)$PBr_2$ groups, —$PCl_2$ groups or —$PBr_2$ groups and then removing the borane group to form a compound of the formula VIII,

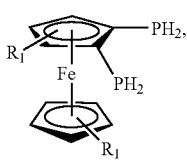
(VIII)

or c) reaction of a compound of the formula VI with a sec-phosphine halide to form a compound of the formula IX,

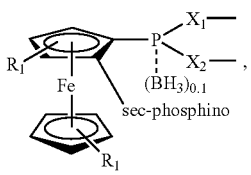
(IX)

c1) removing any borane group present from a compound of the formula IX, then splitting off the radicals (hetero)hydrocarbon-$X_1$, (hetero)hydrocarbon-$X_2$ or $X_1$-(hetero)hydrocarbon-$X_2$ by means of HCl or HBr to form a —$PCl_2$ group or —$PBr_2$ group and then hydrogenating the —$PCl_2$ groups or —$PBr_2$ groups to form a compound of the formula X or c2) splitting off the radicals (hetero)hydrocarbon-$X_1$, (hetero)hydrocarbon-$X_2$ or $X_1$- hetero)-hydrocarbon-$X_2$ from a compound of the formula IX by means of HCl or HBr to form a —$PCl_2$ group or —$PBr_2$ group and then hydrogenating the —$PCl_2$ groups or —$PBr_2$ groups and then removing the borane group to form a compound of the formula X

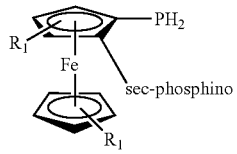
(X)

or d) reaction of a compound of the formula VI with a halogenating reagent to form a compound of the formula XI

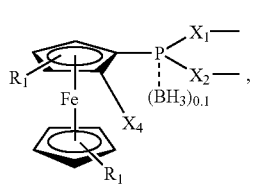
(XI)

where $X_4$ is Cl, Br or I, d1) removing any borane group present from a compound of the formula XI, then splitting off the radicals (hetero)hydrocarbon-$X_1$,(hetero)hydrocarbon-$X_2$ or $X_1$ -(hetero)hydrocarbon-$X_2$ by means of HCl or HBr to form a —$PCl_2$ group or —$PBr_2$ group and then hydrogenating the —$PCl_2$ group or —$PBr_2$ group to form a compound of the formula XII or d2) splitting off the radicals (hetero)hydrocarbon-$X_1$, (hetero)hydrocarbon-$X_2$ or $X_1$-(hetero)-hydrocarbon-$X_2$ from a compound of the formula XI by means of HCl or HBr to form a —$PCl_2$ group or —$PBr_2$ group and then hydrogenating the —$PCl_2$ groups or —$PBr_2$ groups and then removing the borane group to form a compound of the formula XII

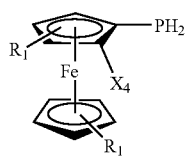
(XII)

and d3) reacting the compound of the formula XII with a metalated sec-phosphine to form a compound of the formula X, e) reaction of the compound of the formula VII with at least 2 equivalents and of the compound of the formula X with at least 1 equivalent of a cyclic sulfate or an open-chain disulfonate to produce compounds of the formula I in which one or both sec-phosphino groups are cyclic sec-phosphino or f) reaction of a compound of the formula XII with at least 1 equivalent of a cyclic sulfate or an open-chain disulfonate to produce compounds of the formula XIII,

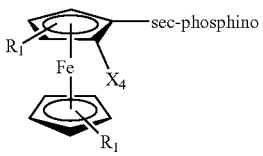

(XIII)

where sec-phosphino is cyclic sec-phosphino which may, if appropriate, be protected by $BH_3$, and then reaction of a compound of the formula XIII with at least 1 equivalent of a lithium alkyl and then with at least 1 equivalent of a sec-phosphine halide to form a compound of the formula I.

Aliphatic Li sec-amide or $X_3Mg$ sec-amide in step a) can be derived from secondary amines containing from 2 to 18, preferably from 2 to 12 and particularly preferably from 2 to 10, carbon atoms. The aliphatic radicals bound to the N atom can be alkyl, cycloalkyl or cycloalkylalkyl or be N-heterocyclic rings having from 4 to 12 and preferably from 5 to 7 carbon atoms. Examples of radicals bound to the N atom are methyl, ethyl, n-propyl, n-butyl, pentyl, hexyl, cyclopentyl, cyclohexyl and cyclohexylmethyl. Examples of N-heterocyclic rings are pyrrolidine, piperidine, morpholine, N-methylpiperazine, 2,2,6,6-tetramethyl-piperidine and azanorbornane. In a preferred embodiment, the amides correspond to the formula $Li—N(C_1-C_4-alkyl)_2$ or $X_3Mg—N(C_1-C_4-alkyl2$, where alkyl is, in particular, methyl.

In the compounds of the formula V, $X_1$ and $X_2$ are preferably N.

For the purposes of the invention, the following hydrocarbon or heterohydrocarbon radicals, for example, can be bound to the groups $X_1$ and $X_2$:

a monovalent (hetero)hydrocarbon radical is bound to each of $X_1$ and $X_2$ or a divalent (hetero)hydrocarbon radical is bound to $X_1$ and $X_2$ when $X_1$ and $X_2$ are O;

two monovalent (hetero)hydrocarbon radicals are bound to each of $X_1$ and $X_2$ when $X_1$ and $X_2$ are N;

two divalent (hetero)hydrocarbon radicals are bound to each of $X_1$ and $X_2$ when $X_1$ and $X_2$ are N, with the divalent (hetero)hydrocarbon radicals being able to be bridged by a bond, methylene or ethylene;

a divalent (hetero)hydrocarbon radical is bound to $X_1$ and two monovalent radicals are bound to $X_2$ when $X_1$ and $X_2$ are N, with a monovalent radical being methylene or ethylene bound to the divalent (hetero)hydrocarbon radical;

a monovalent (hetero)hydrocarbon radical is bound to each of $X_1$ and $X_2$ and a divalent (hetero)hydrocarbon radical is bound to each of $X_1$ and $X_2$ when $X_1$ and $X_2$ are N;

two monovalent (hetero)hydrocarbon radicals are bound to $X_1$ and a divalent (hetero)hydrocarbon radical is bound to $X_2$ when $X_1$ and $X_2$ are N;

two divalent (hetero)hydrocarbon radicals are bound to each of $X_1$ and $X_2$ when $X_1$ and $X_2$ are N;

$X_1$ is O and a monovalent (hetero)hydrocarbon radical is bound to $X_1$ and $X_2$ is N and two monovalent (hetero) hydrocarbon radicals or a divalent (hetero)hydrocarbon radical are/is bound to $X_2$;

$X_1$ is O and $X_2$ is N and a divalent (hetero)hydrocarbon radical is bound to $X_1$ and $X_2$ and a monovalent (hetero) hydrocarbon radical is bound to $X_2$;

a divalent, aromatic 1,1'-(hetero)hydrocarbon radical is bound to $X_1$ and $X_2$ when $X_1$ and $X_2$ are O; or a divalent, aromatic 1,1'-(hetero)hydrocarbon radical is bound to $X_1$ and $X_2$ and a monovalent (hetero)hydrocarbon radical is bound to each of $X_1$ and $X_2$ when $X_1$ and $X_2$ are N.

Hydrocarbon or heterohydrocarbon radicals bound via carbon to $X_1$ and $X_2$ can be a) saturated or unsaturated, straight-chain, branched or cyclic and monovalent radicals, with two monovalent radicals being bound to N atoms $X_1$ and $X_2$;

b) saturated, unsaturated, straight-chain, branched and/or cyclic or bicyclic divalent radicals which are bound to $X_1$ and/or $X_2$ when $X_1$ and $X_2$ are N and form a 4- to 7-membered ring or c) saturated, unsaturated, straight-chain, branched and/or cyclic or bicyclic divalent radicals which form a single or double bridge between an O atom and N atom or the two N atoms and together with the group $—X_1—P—X_2—$ form a 5- to 7-membered ring.

Heterohydrocarbon radicals can contain heteroatoms selected from the group consisting of O, S and $N(C_1-C_4-alkyl)$. The number of heteroatoms is preferably from 1 to 4, more preferably from 1 to 3 and particularly preferably 1 or 2. The hydrocarbon or heterohydrocarbon radicals can contain from 1 to 18, preferably from 1 to 12 and particularly preferably from 1 to 8, carbon atoms and, if appropriate, heteroatoms. The radicals can be monosubstituted or polysubstituted, preferably monosubstituted to trisubstituted or monosubstituted or disubstituted, for example by phenyl, phenoxy, benzyl, benzyloxy, $C_1-C_4$-alkylphenyl, $C_1-C_4$-alkylphenoxy, $C_1-C_4$-alkylbenzyl, $C_1-C_4$-alkylbenzyloxy, $C_1-C_4$-alkoxyphenyl, $C_1-C_4$-alkoxyphenoxy, $C_1-C_4$-alkoxybenzyl, $C_1-C_4$-alkoxybenzyloxy, $C_1-C_4$-alkylthiophenyl, $C_1-C_4$-alkylthiophenoxy, $C_1-C_4$-alkylthiobenzyl, $C_1-C_4$-alkylthiobenzyloxy, $di(C_1-C_4-alkyl)aminophenyl$, $di(C_1-C_4-alkyl)aminophenoxy$, cyclohexyl, cyclopentyl, $C_1-C_4$-alkylcyclohexyl, $C_1-C_4$-alkylcyclopentyl, $C_1-C_4$-alkoxycyclohexyl, $C_1-C_4$-alkoxycyclopentyl, fluorine, $C_1-C_4$-alkyl, $C_1-C_4$-fluoroalkyl, $C_1-C_4$-alkoxy, $C_1-C_4$-alkylthio, $di(C_1-C_4-alkyl)amino$, $C_1-C_4$-alkoxy-$C_1-C_4$-alkyl, $C_1-C_4$-alkylthio-$C_1-C_4$-alkyl or $di(C_1-C_4-alkyl)amino-C_1-C_4$-alkyl. Substitution in the α- or β positions relative to the groups $X_1$ and $X_2$ is preferred if the radical has chiral carbon atoms which can bring about optical induction in the metalation and subsequent reactions. Some specific substituents are methyl, ethyl, n- and i-propyl, n-, i- and t-butyl, trifluoromethyl, methoxy, ethoxy, propoxy, i-propoxy, butoxy, i-butoxy, t-butoxy, methylthio, ethylthio, dimethylamino, diethylamino, phenyl, phenoxy, methoxyphenyl and methoxyphenoxy.

Monovalent hydrocarbon or heterohydrocarbon radicals bound via carbon to $X_1$ and $X_2$ can be, for example, unsubstituted or substituted $C_1-C18-$, preferably $C_1-C_{12}-$, and particularly preferably $C_1-C_8$-(hetero)alkyl; unsubstituted or substituted $C_2-C_{18}-$, preferably $C_2-C_{12}-$, and particularly preferably $C_3-C_8$-(hetero)alkenyl; unsubstituted or substituted $C_3-C_{12}-$ and preferably $C_3-C_8$-(hetero)cycloalkyl, unsubstituted or substituted $C_3-C_{12}-$ and preferably $C_3-C_8$-(hetero)cycloalkenyl, unsubstituted or substituted $C_3-Cl_2-$ and preferably $C_3-C_8$-(hetero)cycloalkyl-$C_1-C_4$-alkyl, unsubstituted or substituted $C_3-C_{12}-$ and preferably $C_3-C_8$-(hetero)cycloalkenyl-$C_1-C_4$-alkyl, unsubstituted or substituted $C_6-C_{14}$-(hetero)aryl and $C_6-C_{14}$-(hetero)aryl-$C_1-C_4$-alkyl. Preference is given to saturated and aromatic hydrocarbon or heterohydrocarbon radicals.

Monovalent hydrocarbon radicals can be linear or branched $C_1-C_{12}$-alkyl, preferably $C_1-C_8$-alkyl and particularly preferably $C_1-C_4$-alkyl, $C_3-C_8-$ and preferably $C_4-C_6-$ cycloalkyl, $C_3$-$C_8$-cycloalkyl- and preferably $C_4$-$C_6$-cycloalkyl-methyl or -ethyl, $C_6$-$C_{14}$- and preferably $C_6$-$C_{10}$-aryl, $C_7$-$C_{15}$-aralkyl and preferably $C_7$-$C_{11}$-aralkyl. Some specific examples are methyl, ethyl, n- and i-propyl, n-butyl, pentyl, hexyl, heptyl, octyl, cyclopropyl, cyclobutyl, cyclopentyl, cyclohexyl, cycloheptyl, cyclooctyl, cyclobutylmethyl, cyclopentylmethyl, cyclohexylmethyl, cyclobutylethyl, cyclopentylethyl, cyclohexylethyl, phenyl, naphthyl, benzyl and phenylethyl. If chiral induction is to be achieved, for example in the case of ferrocenes, the hydrocarbon radicals are preferably substituted in the α and/or β position relative to $X_1$ and/or $X_2$, for example by $C_1$-$C_4$-alkyl, $C_1$-$C_4$-alkoxy, ($C_1$-$C_4$-alkyl)$_2$N—, $C_1$-$C_4$-alkoxymethyl, $C_1$-$C_4$-alkoxyethyl, ($C_1$-$C_4$-alkyl)$_2$N-methyl or -ethyl, phenyl, methylphenyl, methoxyphenyl, phenoxy, 2-anisyl, benzyl or benzyloxy.

Some examples of monovalent heterohydrocarbon radicals are $C_1$-$C_8$-alkoxy-$C_2$-$C_4$-alkyl, ($C_1$-$C_4$-alkyl)$_2$N—$C_2$-$C_4$-alkyl, $C_5$-$C_7$-cycloalkoxy-$C_2$-$C_4$-alkyl, $C_4$-$C_{10}$-(hetero)aryloxy-$C_2$-$C_4$-alkyl, $C_4$-$C_7$-heterocycloalkyl-$C_1$-$C_4$-alkyl, $C_4$-$C_{10}$-heteroaryl-$C_1$-$C_4$-alkyl. Some specific examples are methoxyethyl, ethoxyethyl, dimethylaminoethyl, diethylaminoethyl, cyclohexyloxyethyl, phenoxyethyl, N-methylmorpholinylmethyl or N-methylmorpholinylethyl, N-methylpiperidinylmethyl or N-methylpiperidinylethyl, pyridinylmethyl or pyridinylethyl and pyrrolidinylmethyl or pyrrolidinylethyl.

Divalent hydrocarbon radicals which are bound to $X_1$ and $X_2$ when $X_1$ and $X_2$ are each N and together with the N atom form a 4- to 7-membered ring can have from 2 to 8, preferably from 2 to 6 and more preferably from 2 to 4, carbon atoms and are preferably linear or branched, unsubstituted or substituted alkylene onto which aliphatic or aromatic rings may be fused. The hydrocarbon chain can be interrupted by O atoms and/or —N($C_1$-$C_4$-alkyl). Examples of divalent hydrocarbon radicals are trimethylene, tetramethylene, pentamethylene, —(CH$_2$)2—O—(CH$_2$)$_2$—, —(CH$_2$)$_2$—N(CH$_3$)—(CH$_2$)$_2$—, Divalent hydrocarbon radicals together with the atoms to which they are bound form a heterocyclic ring. If chiral induction is to be achieved, for example in the case of ferrocenes, the hydrocarbon radicals are preferably substituted in the α or β position relative to $X_1$ and/or $X_2$, for example by $C_1$-$C_4$-alkyl, $C_1$-$C_4$-alkoxy, $C_1$-$C_4$-alkoxymethyl, $C_1$-$C_4$-alkoxyethyl, —N($C_1$-$C_4$-alkyl), ($C_1$-$C_4$-alkyl)$_2$N-methyl or -ethyl, phenyl, 2-anisyl or benzyl. If two N atoms are bridged by two divalent radicals, these radicals are derived from cyclic diamines, for example piperazine.

Divalent hydrocarbon radicals which are bound to $X_1$ and $X_2$ when $X_1$ and $X_2$ are each N are preferably derived from 1,2- or 1,3-diamines, with an amino group being able to be part of a ring. The radicals can be linear or branched 1,2- or 1,3-$C_2$-$C_{12}$-alkylene, preferably 1,2- or 1,3-$C_2$-$C_8$-alkylene and particularly preferably 1,2- or 1,3-$C_2$-$C_4$-alkylene, 1,2- or 1,3-$C_3$-$C_8$- and preferably 1,2- or 1,3-$C_4$-$C_6$-cycloalkylene, 1-$C_3$-$C_8$-cycloalkyl- and preferably 1-$C_4$-$C_6$-cycloalkyl-2-methylene or -ethylene, $C_6$-$C_{14}$- and preferably 1,2-$C_6$-$C_{10}$-arylene and $C_6$-$C_{10}$-aralk-1-yl-2-methylene. Some specific examples are ethylene, n- and i-propylene, n- or i-butylene, cyclopropyl-1,2-ene, cyclobutyl-1,2-ene, cyclopentyl-1,2-ene, cyclohexyl-1,2-ene, cycloheptyl-1,2-ene, cyclooctyl-1,2-ene, cyclobut-1-yl-2-methylene, cyclopent-1-yl-2-methylene, cyclohex-1-yl-2-methylene, cyclobut-1-yl-2-ethylene, cyclopent-1-yl-2-ethylene, cyclohex-1-yl-2-ethylene, 1,2-phenylene, 1,2-naphthylene, phen-1-yl-2-methylene and phen-1-yl-2-ethylene. If chiral induction is to be achieved, for example in the case of ferrocenes, the hydrocarbon radicals are preferably substituted in the α and/or β positions relative to $X_1$ and/or $X_2$, for example by $C_1$-$C_4$-alkyl, $C_1$-$C_4$-alkoxymethyl, $C_1$-$C_4$-alkoxyethyl, —N($C_1$-$C_4$-alkyl), ($C_1$-$C_4$-alkyl)$_2$N-methyl or -ethyl, phenyl, 2-anisyl or benzyl.

Divalent hydrocarbon radicals which are bound to $X_1$ and $X_2$ when $X_1$ and $X_2$ are each N can also be 1,1'-biphenylene, 1,1'-binaphthylene and 1,1'-bispyridine.

Preferred phosphino groups in the formula V correspond to the formulae:

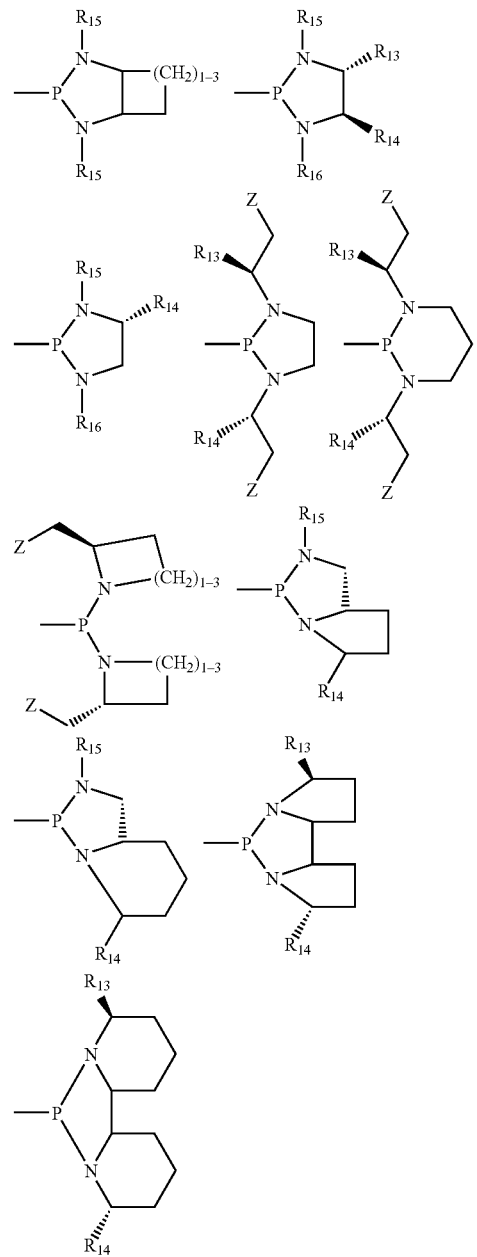

where
$R_{15}$ and $R_{16}$ are identical or different and preferably identical and are each $C_1$-$C_4$-alkyl, $C_1$-$C_4$-alkoxyethyl, ($C_1$-$C_4$-alkyl)$_2$N-ethyl,
$R_{13}$ and $R_{14}$ are identical or different and preferably identical and are each H, $C_1$-$C_4$-alkyl, phenyl or methylphenyl and Z is H, $C_1$-$C_4$-alkyl, $C_1$-$C_4$-alkoxy, $C_1$-$C_4$-alkylthio, —N($C_1$-$C_4$-alkyl)$_2$, phenyl, phenoxy, methoxyphenyl or methoxyphenoxy.

Some further examples of Z are methyl, ethyl, methoxy, ethoxy, methylthio and dimethylamino.

Metalations of aromatics are known reactions which are described, for example, by M. Schlosser (Editor) in Organometallics in Synthesis, John Wiley & Sons (1994) or in Jonathan Clayden Organolithiums: Selectivity for Synthesis (Tetrahedron Organic Chemistry Series), Pergamon Press (2002).

For the purposes of the invention, the expression at least equivalent amounts means the use of from 1 to 1.2 equivalents of a magnesium Grignard compound or an aliphatic Li sec-amide or $X_3$Mg sec-amide per reactive =CH— group in the cyclopentadienyl ring.

The reaction is advantageously carried out at low temperatures, for example from 20 to −100° C., preferably from 0 to −80° C. The reaction time is from about 2 to 5 hours. The reaction is advantageously carried out under an inert protective gas, for example nitrogen or noble gases such as argon.

The reaction is advantageously carried out in the presence of inert solvents. Such solvents can be used either alone or as combinations of at least two solvents. Examples of solvents are aliphatic, cycloaliphatic and aromatic hydrocarbons and open-chain or cyclic ethers. Specific examples are petroleum ether, pentane, hexane, heptane, cyclohexane, methylcyclohexane, benzene, toluene, xylene, diethyl ether, dibutyl ether, tert-butyl methyl ether, ethylene glycol dimethyl or diethyl ether, tetrahydrofuran and dioxane.

Compounds of the formula V are known or can be prepared by known methods or methods analogous to known methods. For example, monolithiated ferrocenes are used as starting materials and are reacted with monohalophosphines of the formula $X_5$P($X_1$—)$X_2$—, where $X_5$ is preferably Cl or Br, $X_1$ and $X_2$ are O or N and a hydrocarbon radical is bound to the free bonds of $X_1$— and $X_2$—. After the reaction, the borane $BH_3$ can, if its presence is desired, be introduced in a known manner, for example by reacting the reaction mixture with a borane complex such as $BH_3$.S($CH_3$)$_2$. Monohalophosphines of the formula $X_5$P($X_1$—)$X_2$— are known or can be obtained in a manner known per se from phosphorus trichloride by reaction with alcohols, diols, amines, amino alcohols or diamines.

Di-sec-aminophosphine halides and dialkoxyphosphine halides and also the di-sec-amino-phosphine (O)halides and dialkoxyphosphine (O)halides used in process step b) are preferably [($C_1$-$C_4$-alkyl)$_2$N]$_2$P—$X_5$, ($C_1$-$C_4$-alkylO)$_2$P—$X_5$, [($C_1$-$C_4$-alkyl)$_2$N]$_2$P(O)—$X_5$ and ($C_1$-$C_4$-alkylO)$_2$P(O)—$X_5$, where $X_5$ is Br and preferably Cl. Some examples of alkyl are methyl, ethyl and propyl, with methyl being particularly preferred. Di-sec-aminophosphine halides and dialkoxyphosphine halides can be protected by borane. The reaction conditions are analogous or similar to the above-described conditions for process step a).

The reactions in process steps b1, b2, c1, c2, d1 and d2 are known per se. Removal of the borane group only in the last reaction step offers the advantage that reaction-sensitive groups remain protected.

The borane group can be split off by, for example, addition of reagents such as secondary amines having $C_1$-$C_4$-alkyl groups, morpholine, 1,8-diazabicyclo[5.4.0]undec-7-ene (DBU), 1,4-diazabicyclo[2.2.2]octane to the dissolved compound of the formula III, sufficiently long stirring at temperatures of from 20 to 100° C. and removal of the volatile constituents, advantageously under reduced pressure. Methods of removal of borane are described, for example, by M. Ohff et al. in Synthesis (1998), page 1391.

The formation of —$PCl_2$ groups or —$PBr_2$ groups is likewise known and is described, for example, by A. Longeau et al. in Tetrahedron: Asymmetry, 8 (1997) pages 987-990. As reagent, it is advantageous to use organic solutions of HCl or HBr in, for example, ethers which are added at low temperatures (for example from −20 to 30° C.) to dissolved compounds of the formula VII, IX or XI with or without a borane group.

—$PCl_2$ groups or —$PBr_2$ groups can be hydrogenated in a manner known per se, for example by means of metal hydrides such as LiH, NaH, KH, Li(AlH$_4$), NaBH$_4$. The reaction is advantageously carried out in the presence of solvents and at temperatures of from −80° C. to 50° C. The primary phosphines obtained can be isolated or be directly reacted further.

The reaction with a sec-phosphine halide as in process step c) is known per se and is described in the examples. The reaction conditions are analogous or similar to the conditions described above for process step a).

The reaction of a compound of the formula VI with a halogenating reagent as in process step d) is likewise known. Suitable halogenating reagents are, for example, $Cl_2$, $Br_2$, $I_2$, interhalogens such as ClBr, BrI or polyhalogenated aliphatic hydrocarbons such as $CF_3$Br, hexachloroethane, $BrCF_2$—$CF_2$Br or 1,1,2,2-tetrabromoethane. The reaction temperature can be from −40° C. to 50° C. Suitable solvents have been mentioned above for process step a). The halogenated compounds obtained can be isolated or be directly used further.

Reactions with a metalated sec-phosphide as in process step d3) are likewise known. A preferred metal is lithium.

The reaction of process step f) is known per se and can be carried out in a manner similar to process step c).

Reactions of primary phosphines with cyclic sulfates have likewise been described, cf. M. J. Burk, J. Amer. Chem. Soc., 1991, 113, 8518-9, M. J. Burk, Acc. Chem. Res., 2000, 33, 363-72 and U. Behrens, M. J. Burk, A. Gerlach, W. Hems, Angew. Chemie, int. Ed., 2000, 112, 2057-2060. Cyclic sulfates are known or can be prepared by analogous methods. The reaction is carried out in solution, for example in ethers. It is advantageous to make concomitant use of equimolar amounts of strong bases, for example Li sec-amides such as lithium diisopropylamide. Reactions with open-chain disulfonates are likewise known and described, for example, by T. V. RajanBabu et al., J. Amer. Chem. Soc. 2001, 123, pages 10207 to 10213. Some examples of sulfonates are di(phenylsulfonates), ditosylates, dimesylates, di(trifluoromethylsulfonates) of open-chain diols.

Isolation and purification of the ferrocene-diphosphines of the invention can be carried out by known methods, for example precipitation and filtration or extraction. Purification can be carried out by distillation, recrystallization or by chromatographic methods.

The ferrocene-diphosphines of the invention are, despite the bulky cyclic sec-phosphino groups, obtained in surprisingly high yields, and one diastereomer is frequently formed preferentially.

The invention also provides the intermediates of the formulae VII, IX and XI involved in the process of the invention,

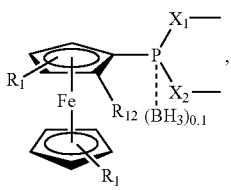

(VII)

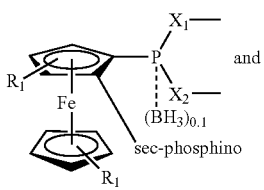

(IX)

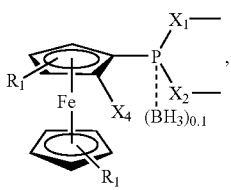

(XI)

where $R_1$, $X_1$, $X_2$, $R_{12}$ and $X_2$ have the abovementioned meanings, including the preferences.

The invention further provides compounds of the formulae VIII, X and XII,

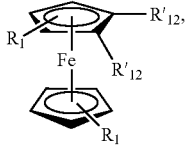

(VIII)

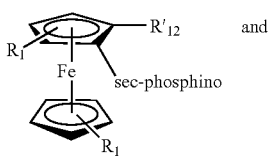

(X)

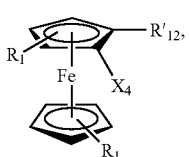

(XII)

where
$R'_{12}$ is —$PCl_2$, —$PBr_2$ or —$PH_2$ and $R_1$ and $X_4$ have the abovementioned meanings, including the preferences.

The invention also provides compounds of the formula XIII

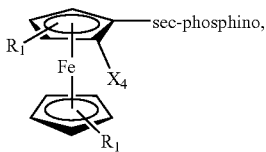

(XIII)

where
$R_1$ and $X_4$ have the abovementioned meanings, including the preferences, and sec-phosphino is cyclic sec-phosphino.

The novel compounds of the formula I are ligands for complexes of metals selected from the group consisting of the group 8 transition metals, in particular from the group consisting of Ru, Rh and Ir, which are excellent catalysts or catalyst precursors for asymmetric syntheses, for example the asymmetric hydrogenation of prochiral, unsaturated, organic compounds. If prochiral unsaturated organic compounds are used, a very high excess of optical isomers can be induced in the synthesis of organic compounds and a high chemical conversion can be achieved in short reaction times. The enantioselectivities and catalyst activities which can be achieved are outstanding.

The invention further provides complexes of metals selected from the group consisting of the transition metals with compounds of the formula I as ligands.

Possible metals are, for example, Cu, Ag, Au, Ni, Co, Rh, Pd, Ir, Ru and Pt. Preferred metals are rhodium and iridium and also ruthenium, platinum and palladium.

Particularly preferred metals are ruthenium, rhodium and iridium.

The metal complexes can, depending on the oxidation number and coordination number of the metal atom, contain further ligands and/or anions. They can also be cationic metal complexes. Such analogous metal complexes and their preparation have been widely described in the literature.

The metal complexes can, for example, correspond to the general formulae XIV and XV, $$A_1MeL_n \quad (XIV),$$

$$(A_1MeL_n)^{(z+)}(E^-)_z \quad (XV),$$

where $A_1$ is a compound of the formula I,
L represents identical or different monodentate, anionic or nonionic ligands, or $L_2$ represents identical or different bidentate, anionic or nonionic ligands;
n is 2, 3 or 4 when L is a monodentate ligand or n is 1 or 2 when L is a bidentate ligand;
z is 1, 2 or 3;
Me is a metal selected from the group consisting of Rh, Ir and Ru; with the metal having the oxidation state 0, 1, 2, 3 or 4;
$E^-$ is the anion of an oxo acid or complex acid; and the anionic ligands balance the charge of the oxidation state 1, 2, 3 or 4 of the metal.

The above-described preferences and embodiments apply to the compounds of the formula I.

Monodentate nonionic ligands can, for example, be selected from the group consisting of olefins (for example ethylene, propylene), allyls (allyl, 2-methallyl), solvating solvents (nitriles, linear or cyclic ethers, unalkylated or N-alkylated amides and lactams, amines, phosphines, alcohols, carboxylic esters, sulfonic esters), nitrogen monoxide and carbon monoxide.

Monodentate anionic ligands can, for example, be selected from the group consisting of halides (F, Cl, Br, I), pseudohalides (cyanide, cyanate, isocyanate) and anions of carboxylic acids, sulfonic acids and phosphonic acids (carbonate, formate, acetate, propionate, methylsulfonate, trifluoromethylsulfonate, phenylsulfonate, tosylate).

Bidentate nonionic ligands can, for example, be selected from the group consisting of linear or cyclic diolefins (for example hexadiene, cyclooctadiene, norbornadiene), dinitriles (malononitrile), unalkylated or N-alkylated carboxamides, diamines, diphosphines, diols, acetonylacetonates, dicarboxylic diesters and disulfonic diesters.

Bidentate anionic ligands can, for example, be selected from the group consisting of the anions of dicarboxylic acids, disulfonic acids and diphosphonic acids (for example of oxalic acid, malonic acid, succinic acid, maleic acid, methylenedisulfonic acid and methylenediphosphonic acid).

Preferred metal complexes also include those in which E is $—Cl^-$, $—Br^-$, $—I^-$, $ClO_4^-$, $CF_3SO_3^-$, $CH_3SO_3^-$, $HSO_4^-$, $(CF_3SO_2)_2N^-$, $(CF_3SO_2)_3C^-$, tetraarylborates such as $B(phenyl)_4^-$, $B[bis(3,5-trifluoromethyl)phenyl]_4^-$, $B[bis(3,5-dimethyl)phenyl]_4^-$, $B(C_6F_5)_4^-$ and $B(4-methylphenyl)_4^-$, $BF_4^-$, $PF_6^-$, $SbCl6^-$, $AsF_6^-$ or $SbF_6^-$.

Very particularly preferred metal complexes which are particularly suitable for hydrogenations correspond to the formulae XIII and XIV,

[A₁Me₂YZ]  (XVI),

[A₁Me₂Y]⁺E₁⁻  (XVII), where
A₁ is a compound of the formula 1;
Me₂ is rhodium or iridium;
Y represents two olefins or diene;
Z is Cl, Br or I; and
E₁⁻ is the anion of an oxo acid or complex acid.

The above-described embodiments and preferences apply to the compounds of the formula I.

Olefins Y can be $C_2-C_{12}$-, preferably $C_2-C_6$- and particularly preferably $C_2-C_4$-olefins. Examples are propene, 1-butene and in particular ethylene. The diene can have from 5 to 12 and preferably from 5 to 8 carbon atoms and can be an open-chain, cyclic or polycyclic diene. The two olefin groups of the diene are preferably connected by one or two CH₂ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5scyclooctadiene and norbornadiene. Y preferably represents two ethylene or 1,5-hexadiene, 1,5-cyclooctadiene or norbornadiene.

In the formula XVI, Z is preferably Cl or Br. Examples of E₁ are $BF_4^-$, $ClO_4^-$, $CF_3SO_3^-$, $CH_3SO_3^-$, $HSO_4^-$, $B(phenyl)_4^-$, $B[bis(3,5-trifluoromethyl)phenyl]_4^-$, $PF_6^-$, $SbCl_6^-$, $AsF_6^-$ or $SbF_6^-$.

The metal complexes of the invention are prepared by methods known in the literature (cf. U.S. Pat. Nos. 5,371,256, 5,446,844, 5,583,241 and E. Jacobsen, A. Pfaltz, H. Yamamoto (Eds.), Comprehensive Asymmetric Catalysis I to III, Springer Verlag, Berlin, 1999, and references cited therein).

The metal complexes of the invention are homogeneous catalysts or catalyst precursors which can be activated under the reaction conditions which can be used for asymmetric addition reactions onto prochiral, unsaturated, organic compounds.

The metal complexes can, for example, be used for the asymmetric hydrogenation (addition of hydrogen) of prochiral compounds having carbon-carbon or carbon-heteroatom multiple bonds, in particular double bonds. Such hydrogenations using soluble homogeneous metal complexes have been described, for example, in Pure and Appl. Chem., Vol. 68, No. 1, pp. 131-138 (1996). Preferred unsaturated compounds to be hydrogenated contain the groups C=C, C=N and/or C=O. According to the invention, complexes of rhodium and iridium are preferably used for the hydrogenation.

The metal complexes of the invention can also be used as catalysts for the asymmetric hydroboration (addition of boron hydrides) of prochiral organic compounds having carbon-carbon double bonds. Such hydroborations are described, for example, by Tamio Hayashi in E. Jacobsen, A. Pfaltz, H. Yamamoto (Eds.), Comprehensive Asymmetric Catalysis I to III, Springer Verlag, Berlin, 1999, pages 351 to 364. Suitable boron hydrides are, for example, catecholboranes. The chiral boron compounds can be used in syntheses and/or be converted in a manner known per se into other chiral organic compounds which represent valuable building blocks for the preparation of chiral intermediates or active substances. An example of such a reaction is the preparation of 3-hydroxytetrahydrofuran (as described in DE 198 07 330).

The metal complexes of the invention can also be used as catalysts for the asymmetric hydrosilylation (addition of silanes) of prochiral organic compounds having carbon-carbon or carbon-heteroatom double bonds. Such hydrosilylations are described, for example, by G. Pioda and A. Togni in Tetrahedron: Asymmetry, 1998, 9, 3093 or by S. Uemura, et al. in Chem. Commun. 1996, 847. Suitable silanes are, for example, trichlorosilane and diphenylsilane. For the hydrosilylation of, for example, C=O and C=N groups, preference is given to using complexes of rhodium and iridium. For the hydrosilylation of, for example, C=C groups, preference is given to using complexes of palladium. The chiral silyl compounds can be used in syntheses and/or be converted in a manner known per se into other chiral organic compounds which represent valuable building blocks for the preparation of chiral intermediates or active substances. Examples of such reactions are hydrolysis to form alcohols.

The metal complexes of the invention can also be used as catalysts for asymmetric allylic substitution reactions (addition of carbon nucleophiles to allyl compounds). Such allylations are described, for example, by A. Pfaltz and M. Lautens in E. Jacobsen, A. Pfaltz, H. Yamamoto (Eds.), Comprehensive Asymmetric Catalysis I to III, Springer Verlag, Berlin, 1999, pages 833 to 884. Suitable precursors for allyl compounds are, for example, 1,3-diphenyl-3-acetoxy-1-propene and 3-acetoxy-1-cyclohexe. Complexes of palladium are preferably used for this reaction. The chiral allyl compounds can be used in syntheses for preparing chiral intermediates or active substances.

The metal complexes of the invention can also be used as catalysts for asymmetric amination (addition of amines onto allyl compounds) or in asymmetric Heck reactions. Such aminations are described, for example, by A. Pfaltz and M. Lautens in E. Jacobsen, A. Pfaltz, H. Yamamoto (Eds.), Comprehensive Asymmetric Catalysis I to III, Springer Verlag, Berlin, 1999, pages 833 to 884, and Heck reactions are described by O. Loiseleur et al. in Journal of Organometallic Chemistry 576 (1999), pages 16 to 22. Suitable amines are ammonia and primary and secondary amines. Preference is given to using complexes of palladium for the amination of allyl compounds. The chiral amines can be used in syntheses for preparing chiral intermediates or active substances.

The invention further provides for the use of the metal complexes of the invention as homogeneous catalysts for preparing chiral organic compounds by asymmetric addition of hydrogen, boron hydrides or silanes onto a carbon-carbon or carbon-heteroatom multiple bond in prochiral organic compounds or asymmetric addition of carbon nucleophiles or amines onto allyl compounds.

A further aspect of the invention is a process for preparing chiral organic compounds by asymmetric addition of hydrogen, boron hydrides or silanes onto a carbon-carbon or carbon-heteroatom multiple bond in prochiral organic compounds or asymmetric addition of carbon nucleophiles or amines onto allyl compounds in the presence of a catalyst, which is characterized in that the addition reaction is carried out in the presence of catalytic amounts of at least one metal complex according to the invention.

Preferred prochiral, unsaturated compounds to be hydrogenated can contain one or more, identical or different $C=C$, $C=N$ and/or $C=O$ groups in open-chain or cyclic organic compounds, with the $C=C$, $C=N$ and/or $C=O$ groups being able to be part of a ring system or being exocyclic groups. The prochiral unsaturated compounds can be alkenes, cycloalkenes, heterocycloalkenes and open-chain or cyclic ketones, ketimines and kethydrazones. They can, for example, correspond to the formula X, $$R_{07}R_{08}C=D \quad (XVIII),$$

where $R_{07}$ and $R_{08}$ are selected so that the compound is prochiral and are each, independently of one another, an open-chain or cyclic hydrocarbon radical or heterohydrocarbon radical containing heteroatoms selected from the group consisting of O, S and N, which has from 1 to 30 and preferably from 1 to 20 carbon atoms;

D is O or a radical of the formula $C=R_{09}R_{010}$ or $NR_{011}$;

$R_{09}$ and $R_{010}$ independently have one of the meanings of $R_{07}$ and $R_{08}$, $R_{011}$ is hydrogen, $C_1$-$C_{12}$-alkyl, $C_1$-$C_{12}$-alkoxy, $C_3$-$C_{12}$-cycloalkyl, $C_3$-$C_{12}$-cycloalkyl-$C_1$-$C_6$-alkyl, $C_3$-$C_{11}$-heterocycloalkyl, $C_3$-$C_{11}$-heterocycloalkyl-$C_1$-$C_6$-alkyl, $C_6$-$C_{14}$-aryl, $C_5$-$C_{13}$-heteroaryl, $C_7$-$C_{16}$-aralkyl or $C_6$-$C_{14}$-heteroaralkyl, $R_{07}$ and $R_{08}$ together with the carbon atom to which they are bound form a hydrocarbon ring or heterohydrocarbon ring having from 3 to 12 ring atoms;

$R_{07}$ and $R_{08}$ in each case together with the $C=C$ group to which they are bound form a hydrocarbon ring or heterohydrocarbon ring having from 3 to 12 ring atoms;

$R_{07}$ and $R_{011}$ in each case together with the $C=N$ group to which they are bound form a hydrocarbon ring or heterohydrocarbon ring having from 3 to 12 ring atoms;

the heteroatoms in the heterocyclic rings are selected from the group consisting of O, S and N;

and $R_{07}$, $R_{08}$, $R_{09}$, $R_{010}$ and $R_{011}$, are unsubstituted or substituted by $C_1$-$C_6$-alkyl, $C_1$-$C_6$-alkoxy, cyclohexyl, $C_6$-$C_{10}$-aryl, $C_7$-$C_{12}$-aralkyl, $C_1$-$C_4$-alkyl-$C_6$-$C_{10}$-aryl, $C_1$-$C_4$-alkoxy-$C_6$-$C_{10}$-aryl, $C_1$-$C_4$-alkyl-$C_7$-$C_{12}$-aralkyl, $C_1$-$C_4$-alkoxy-$C_7$-$C_{12}$-aralkyl, —OH, =O, —CO—$OR_{012}$, —CO—$NR_{013}R_{014}$ or —$NR_{013}R_{014}$, where $R_{012}$ is H, an alkali metal, $C_1$-$C_6$-alkyl, cyclohexyl, phenyl or benzyl and $R_{013}$ and $R_{014}$ are each, independently of one another, hydrogen, $C_1$-$C_6$-alkyl, cyclohexyl, phenyl or benzyl or $R_{013}$ and $R_{014}$ together form tetramethylene, pentamethylene or 3-oxapentylene.

Examples and preferences for substituents have been mentioned above. $R_{07}$ and $R_{08}$ can be, for example, $C_1$-$C_{20}$-alkyl and preferably $C_1$-$C_{12}$-alkyl, $C_1$-$C_{20}$-heteroalkyl and preferably $C_1$-$C_{12}$-heteroalkyl containing heteroatoms selected from the group consisting of O, S and N, $C_3$-$C_{12}$-cycloalkyl and preferably $C_4$-$C_8$-cycloalkyl, C-bonded $C_3$-$C_{11}$-heterocycloalkyl and preferably $C_4$-$C_8$-heterocycloalkyl containing heteroatoms selected from the group consisting of O, S and N, $C_3$-$C_{12}$-cycloalkyl-$C_1$-$C_6$-alkyl and preferably $C_4$-$C_8$-cycloalkyl-$C_1$-$C_6$-alkyl, $C_3$-$C_{11}$-heterocycloalkyl-$C_1$-$C_6$-alkyl and preferably $C_4$-$C_8$-heterocycloalkyl-$C_1$-$C_6$-alkyl containing heteroatoms selected from the group consisting of O, S and N, $C_6$-$C_{14}$-aryl and preferably $C_6$-$C_{10}$-aryl, $C_5$-$C_{13}$-heteroaryl and preferably $C_5$-$C_9$-heteroaryl containing heteroatoms selected from the group consisting of O, S and N, $C_7$-$C_{15}$-aralkyl and preferably $C_7$-$C_{11}$-aralkyl, $C_6$-$C_{12}$-heteroaralkyl and preferably $C_6$-$C_{10}$-heteroaralkyl containing heteroatoms selected from the group consisting of O, S and N.

When $R_{07}$ and $R_{08}$, $R_{07}$ and $R_{09}$, or $R_{07}$ and $R_{011}$, in each case together with the group to which they are bound form a hydrocarbon ring or heterohydrocarbon ring, the ring preferably has from 4 to 8 ring atoms. The heterohydrocarbon ring can, for example, contain from 1 to 3 and preferably one or two heteroatoms.

$R_{011}$ is preferably hydrogen, $C_1$-$C_6$-alkyl, $C_1$-$C_6$-alkoxy, $C_4$-$C_8$-cycloalkyl, $C_4$-$C_8$-cycloalkyl-$C_1$-$C_4$-alkyl, $C_4$-$C_{10}$-heterocycloalkyl, $C_4$-$C_{10}$-heterocycloalkyl-$C_1$-$C_4$-alkyl, $C_6$-$C_{10}$-aryl, $C_5$-$C_9$-heteroaryl, $C_7$-$C_{12}$-aralkyl or $C_5$-$C_{13}$-heteroaralkyl.

Some examples of unsaturated organic compounds are acetophenone, 4-methoxyacetophenone, 4-trifluoromethylacetophenone, 4-nitroacetophenone, 2-chloroacetophenone, corresponding unsubstituted or N-substituted acetophenone benzylimines, unsubstituted or substituted benzocyclohexanone or benzocyclopentanone and corresponding imines, imines from the group consisting of unsubstituted or substituted tetrahydroquinoline, tetrahydropyridine and dihydropyrrole, and unsaturated carboxylic acids, carboxylic esters, carboxamides and carboxylic salts such as α- and possibly β-substituted acrylic acids or crotonic acids. Preferred carboxylic acids are acids of the formula $$R_{012}\text{—CH}=C(R_{013})\text{—C(O)OH}$$

and also its salts, esters and amides, where $R_{012}$ is $C_1$-$C_6$-alkyl, unsubstituted $C_3$-$C_8$-cycloalkyl or $C_3$-$C_8$-cycloalkyl substituted by from 1 to 4 $C_1$-$C_6$-alkyl, $C_1$-$C_6$-alkoxy, $C_1$-$C_6$-alkoxy-$C_1$-$C_4$-alkoxy groups or unsubstituted $C_6$-$C_{10}$-aryl, preferably phenyl, or $C_6$-$C_{10}$-aryl, preferably phenyl, substituted by from 1 to 4 $C_1$-$C_6$-alkyl, $C_1$-$C_6$-alkoxy, $C_1$-$C_6$-alkoxy-$C_1$-$C_4$-alkoxy groups and $R_{013}$ is linear or branched $C_1$-$C_6$-alkyl (for example isopropyl), unsubstituted cyclopentyl, cyclohexyl or phenyl or cyclopentyl, cyclohexyl or phenyl substituted as defined above or protected amino (for example acetylamino).

The process of the invention can be carried out at low or elevated temperatures, for example temperatures of from −20 to 150° C., preferably from −10 to 100° C. and particularly preferably from 10 to 80° C. The optical yields are generally better at low temperature than at higher temperatures.

The process of the invention can be carried out at atmospheric pressure or superatmospheric pressure. The pressure can be, for example, from $10^5$ to $2 \times 10^7$ Pa (pascal). Hydrogenations can be carried out at atmospheric pressure or at superatmospheric pressure. Better selectivities are frequently observed at atmospheric pressure.

Catalysts are preferably used in amounts of from 0.0001 to 10 mol %, particularly preferably from 0.001 to 10 mol % and in particular from 0.01 to 5 mol %, based on the compound to be hydrogenated.

The preparation of the ligands and catalysts and also the addition reaction can be carried out without solvents or in the presence of an inert solvent, with one solvent or mixtures of solvents being able to be used. Suitable solvents are, for example, aliphatic, cycloaliphatic and aromatic hydrocarbons (pentane, hexane, petroleum ether, cyclohexane, methylcyclohexane, benzene, toluene, xylene), aliphatic halogenated hydrocarbons (methylene chloride, chloroform, dichloroethane and tetrachloroethane), nitriles (acetonitrile, propionitrile, benzonitrile), ethers (diethyl ether, dibutyl ether, t-butyl methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactones), N-substituted lactams (N-methylpyrrolidone), carboxamides (dimethylamide, dimethylformamide), acyclic ureas (dimethylimidazoline) and sulfoxides and sulfones (dimethyl sulfoxide, dimethyl sulfone, tetramethylene sulfoxide, tetramethylene sulfone) and alcohols (methanol, ethanol, propanol, butanol, ethylene glycol monomethyl ether, ethylene glycol monoethyl ether, diethylene glycol monomethyl ether) and water. The solvents can be used alone or as mixtures of at least two solvents.

The reaction can be carried out in the presence of cocatalysts, for example quaternary ammonium halides (tetrabutylammonium iodide), and/or in the presence of protic acids, for example mineral acids (cf., for example U.S. Pat. Nos. 5,371,256, 5,446,844 and 5,583,241 and EP-A-0 691 949). The cocatalysts are particularly useful for hydrogenations.

The metal complexes used as catalysts can be added as separately prepared isolated compounds or can alternatively be formed in situ prior to the reaction and then be mixed with the substrate to be hydrogenated. It can be advantageous for ligands to be additionally added during the reaction when using isolated metal complexes or to use an excess of the ligands in the case of the in-situ preparation. The excess can, for example, be from 1 to 10 mol and preferably from 1 to 5 mol, based on the metal compound used for the preparation.

The process of the invention is generally carried out by initially charging the catalyst and then adding the substrate, if appropriate reaction auxiliaries and the compound to be added on, and subsequently starting the reaction. Gaseous compounds to be added on, for example hydrogen or ammonia, are advantageously introduced under pressure. The process can be carried out continuously or batchwise in various types of reactor.

The chiral organic compounds which can be prepared according to the invention are active substances or intermediates for the preparation of such substances, in particular in the field of production of pharmaceuticals and agrochemicals.

The following examples illustrate the invention.

A) Preparation of Halophosphines

All reactions are carried out in dried solvents and under inert gas.

EXAMPLE A1

Preparation of

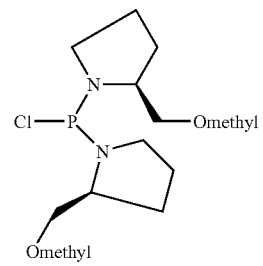

In a 500 ml round-bottom flask provided with an argon inlet, $PCl_3$ (7.38 g, 53.75 mmol) is dissolved in dry tetrahydrofuran (THF, 150 ml) under argon and the solution is cooled to 0° C. in an ice bath. Triethylamine (11.97 g, 118.25 mmol, 2.20 equivalents) is added dropwise and (S)methoxymethylpyrrolidine (12.69 g, 110.19 mmol, 2.05 equivalents) is then slowly added dropwise. During the addition, formation of a white precipitate is observed. The ice bath is removed and the suspension obtained is stirred overnight (14 h) at room temperature (RT). The white precipitate formed is filtered off by means of a double-ended frit filter and washed with dry THF (2×25 ml). A $^{31}$P-NMR ($C_6D_6$) spectrum of the yellowish filtrate obtained is recorded. The solution obtained in this way is reacted without further purification. $^{31}$P-NMR ($C_6D_6$, 121 MHz): 154.3 (s).

EXAMPLE A2

Preparation of

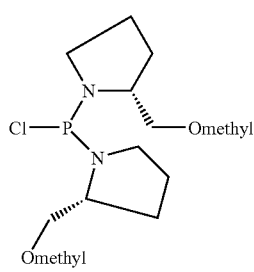

The procedure of example A1 is repeated using (R)-methoxymethylpyrrolidine.

B) Preparation of Aromatic Monophosphines

EXAMPLE B1

Preparation of

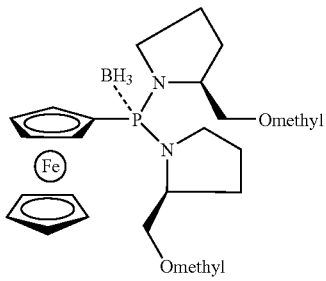

In a 1 l round-bottom flask provided with an argon inlet, ferrocene (10.00 g, 53.75 mmol) and potassium tert-butoxide (754 mg, 6.72 mmol, 0.125 equivalent) is dissolved in dry THF (100 ml) under argon. The solution is cooled to −78° C. and t-butyllithium (1.5 M in hexane; 71.67 ml, 107.50 mmol, 2.00 equivalents) is added dropwise over a period of 45 minutes. The solution is stirred at −78° C. for 1.5 hours and admixed with n-heptane (75 ml). After the precipitate obtained has settled, the supernatant solution is removed at −78° C. by means of a cannula under argon pressure. The precipitate is washed at −78° C. with n-heptane (60 ml) and the washings are once again removed by means of a cannula under argon pressure. This procedure is repeated three times. The precipitate obtained is dissolved in dry THF (50 ml) and a solution of A1 (53.75 mmol, 1.00 equivalent) in THF (200 ml) is added dropwise at −78° C. over a period of 1.5 hours. The solution is stirred overnight (14 h) while warming to RT. Borane-dimethylsulfide complex (5.10 ml, 53.75 mmol, 1.00 equivalent) is subsequently added dropwise and the mixture is stirred overnight at RT. The reaction mixture is hydrolyzed with saturated NH$_4$Cl solution (50 ml) and extracted with tert-butyl methyl ether (TBME) (3×100 ml). The combined organic phases are dried over Na$_2$SO$_4$ and the solvent is distilled off on a rotary evaporator. The crude product (24.18 g) is purified by column chromatography (200 g of silica gel, n-heptane/TBME 5:1). The title compound (17.23 g, 70% of theory) is obtained as an orange solid. $^{31}$P-NMR (C$_6$D$_6$, 121 MHz): 80.8 (m, broad).

EXAMPLE B2

Preparation of

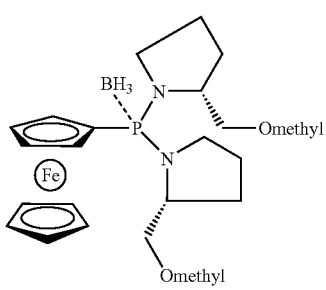

The procedure of example B1 is repeated using the compound A2 in place of A1.

EXAMPLE B3

Preparation of

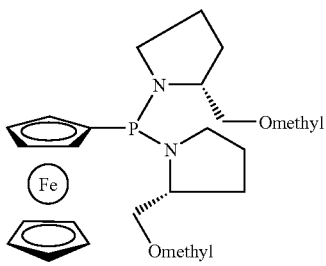

17.9 mmol of a 1.6 molar n-butyllithium solution in hexane are slowly added dropwise to a solution of 4.53 g (17.1 mmol) of bromoferrocene in 15 ml of THF at −78° C. and the mixture is stirred at this temperature for 10 minutes. The temperature is then allowed to rise to 0-5° C. (ice cooling), a solution of 18.8 mmol of the compound of example A2 in 78 ml of THF is added dropwise and the mixture is stirred overnight at RT. The solvent is subsequently taken off and the crude product is purified on a short column (silica gel 60 from Fluka, eluent: TBME). Distillation of the colored fractions on a rotary evaporator gives an orange, almost solid, oil. $^{31}$P-NMR (C$_6$D$_6$, 121 MHz): 70.7 (s).

C) Preparation of Primary Ferrocene-phosphines

EXAMPLE C1

Preparation of Ferrocene-1,2-diphosphine

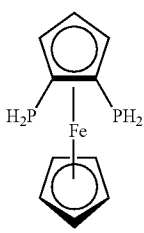

a) Preparation of

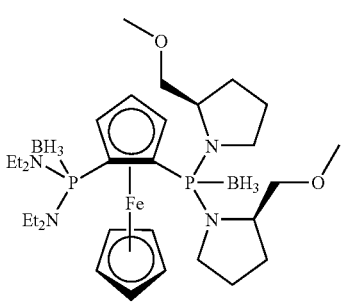

Et = ethyl

In a 50 ml round-bottom flask provided with an argon inlet, the compound of example B2 (1.00 g, 2.18 mmol) is dissolved in dry tert-butyl methyl ether (TBME) (5.00 ml)

and n-hexane (5.00 ml) and the solution obtained is cooled to −30° C. This results in precipitation of the starting material as a yellow solid. s-Butyllithium (1.3 M in cyclohexane; 1.76 ml, 2.29 mmol, 1.05 equivalents) is added dropwise. During this addition, the yellow solid gradually goes into solution, the solution becomes orange-red and after about 30 minutes an orange solid precipitates. After stirring at −30° C. for 2 hours, ClP(Nethyl$_2$)$_2$ (551 mg, 2.62 mmol, 1.2 equivalents) is added, the cooling bath is removed and the suspension is stirred for 2 hours while warming to room temperature (RT). BH$_3$.SMe$_2$ (0.25 ml, 2.62 mmol, 1.2 equivalents) is subsequently added dropwise and the suspension is stirred overnight (14 h) at RT. The reaction mixture is hydrolyzed with saturated NaCl solution (50 ml), TBME (50 ml) is added, the organic phase is separated off and dried over Na$_2$SO$_4$. The solvent is distilled off on a rotary evaporator and the crude product is purified by column chromatography (100 g of silica gel, n-heptane/TBME 5:1). The ferrocenyl compound (1.10 g, 1.71 mmol, 78%) is obtained in the form of an orange solid. $^{31}$P-NMR (C$_6$D$_6$, 121 MHz): 99.7-99.0 (m, br), 79.9-79.5 (m, br).

b) Preparation of

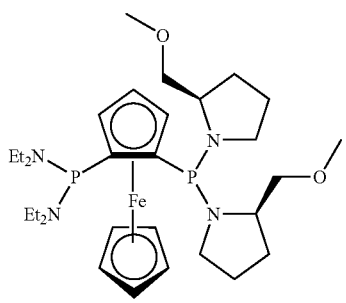

To remove the borane group, 1.00 g (1.87 mmol) of the compound prepared as described in a) are taken up in 5 ml of diethylamine and stirred overnight at 50° C. All volatile constituents are subsequently removed at 50° C. in an oil pump vacuum. The residue obtained is taken up three times in diethylamine (2.00 ml each time), stirred at 50° C. for 30 minutes and all volatile constituents are removed at 50° C. in an oil pump vacuum (30 minutes). The residue is taken up twice in dry TBME (2 ml) and all volatile constituents are removed at 50° C. in an oil pump vacuum. The product with the protection removed remains and is used further in step c) without purification. $^{31}$P-NMR (C$_6$D$_6$, 121 MHz): −151 ppm.

c) Preparation of

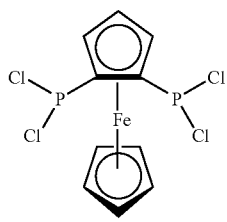

The reaction product prepared as described in b) is dissolved in 5 ml of TBME and, at 0° C., 8 mmol of an HCl solution (2N in diethyl ether) are added dropwise while stirring. The reaction solution is subsequently separated off from the precipitate in ammonium compounds by decantation and volatile constituents are removed under argon on a rotary evaporator. The residue is used directly in step d). $^{31}$P-NMR (C$_6$D$_6$, 121 MHz): 156.5 (s)

d) Preparation of the Title Compound 0.43 g (11.20 mmol) of lithium aluminum hydride is suspended in 10 ml of absolute tetrahydrofuran (THF) under argon and cooled to −78° C. The crude product obtained as described in c) is dissolved in 5 ml of absolute THF and added dropwise to the cooled suspension of the lithium aluminum hydride. The reaction mixture is stirred at this temperature for 30 minutes and then at 20° C. for 30 minutes. 3.8 ml of 2N NaOH are added dropwise to the suspension and the supernatant solution is filtered off and evaporated to isolate the title compound. $^{31}$P-NMR (C$_6$D$_6$, 121 MHz): −151 ppm.

EXAMPLE C2

Preparation of

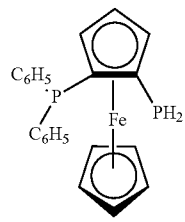

C2

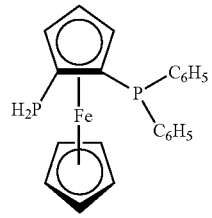

C2' a) Preparation of

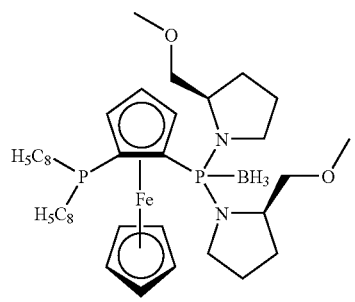

9.5 mmol of sec-butyllithium (1.3 molar in hexane) are added dropwise to a solution of 4.05 g (8.80 mmol) of the compound of example B2 in 60 ml of hexane/TBME 1:1 at −40° C. The reaction mixture is stirred further at this temperature for 2 hours. 9.43 mmol of chlorodiphenylphosphine are subsequently added to the resulting orange suspension. The reaction mixture is then allowed to warm slowly to room temperature while stirring. After stirring for 2 hours overnight, the mixture is extracted with water/methylene chloride, the organic phases are dried over sodium sulfate and the solvent is distilled off under reduced pressure on a rotary evaporator. Purification by column chromatography (silica gel 60, eluent=hexane/TBME 6:1) gives the desired product as orange crystalline material in a yield of 85%. $^{31}$P-NMR ($C_6D_6$, 121 MHz): −25.2 (s), +79 (s, broad). 1H-NMR ($C_6D_6$, 300 MHz), characteristic signals: 7.80 (m), 7.37 (m), 6.97-7.16 (m), 4.08 (s, 5H, cyclopentadiene ring), 3.28 (s, 3H, O—$CH_3$), 3.10 (s, 3H, O—$CH_3$).

b) Preparation of

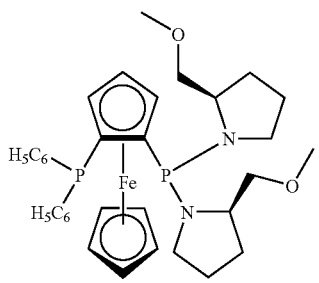

To remove the borane group, 400 mg (0.62 mmol) of the compound prepared as described in a) are taken up in 5 ml of diethylamine and stirred overnight at 50° C. All volatile constituents are subsequently removed at 50° C. in an oil pump vacuum. The residue obtained is taken up three times in diethylamine (2.00 ml each time), stirred at 50° C. for 30 minutes and all volatile constituents are removed at 50° C. in an oil pump vacuum (30 minutes). The residue is taken up twice in dry TBME (2 ml) and all volatile constituents are removed at 50° C. in an oil pump vacuum. The $BH_3$-freeproduct remains and is used further in step c) without purification. $^{31}$P-NMR ($C_6D_6$, 121 MHz): −23.5 (d, $J_{PP}$~73 Hz), +69.4 (d, $J_{PP}$~73 Hz).

c) Preparation of

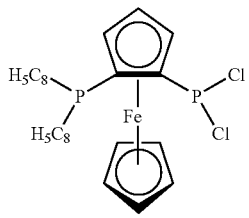

The reaction product prepared as described in b) is dissolved in 5 ml of TBME and, at 0° C., 2.6 mmol of an HCl solution (2N in diethyl ether) is added dropwise while stirring. The reaction solution is subsequently separated off from the precipitated ammonium compounds by decantation and volatile constituents are removed under argon on a rotary evaporator. The residue is used directly in step d). $^{31}$P-NMR ($C_6D_6$, 121 MHz): −23.6 (d, $J_{PP}$~170 Hz), +161.6 (d, $J_{PP}$~170 Hz).

d1) Preparation of the Title Compound C2

2 mmol of lithium aluminum hydride are suspended in 3 ml of absolute THF under argon and cooled to −78° C. The crude product prepared as described in c) is dissolved in 3 ml of absolute THF and added dropwise to the cooled suspension of lithium aluminum hydride. The reaction mixture is stirred at this temperature for 30 minutes and then at 20° C. for 30 minutes. 0.8 ml of 2N NaOH is added dropwise to the suspension and the supernatant solution is filtered off and evaporated to isolate the title compound. $^{31}$P-NMR ($C_6D_6$, 121 MHz): −20 (m,), −152 (m).

d2) Preparation of the Title Compound C2'

The procedure of example C2 is repeated using the compound B1 in place of B2 in step a).

EXAMPLE C3

Preparation of

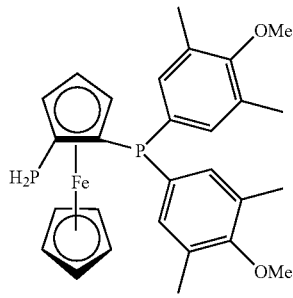

a) Preparation of

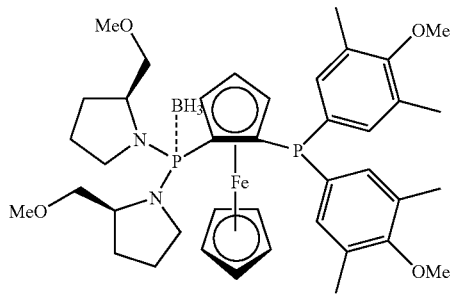

9.43 mmol of sec-butyllithium (1.3 molar in hexane) are added dropwise to a solution of 4 g (8.70 mmol) of the compound of example B1 in 60 ml of hexane/TBME 1:1 at −40° C. The reaction mixture is stirred further at this temperature for 2 hours. 9.43 mmol of bis(3,5-di-methyl-4-methoxyphenyl)phosphine chloride are subsequently added to the resulting orange suspension. The reaction mixture is then allowed to warm slowly to room temperature while stirring. After stirring for 2 hours, the mixture is extracted with water/TBME, the organic phases are dried over sodium sulfate and the solvent is distilled off under reduced pressure on a rotary evaporator. Purification by column chromatography gives the desired product as a yellow crystalline material in a yield of 74%. $^{31}$P-NMR (C$_6$D$_6$, 121 MHz): −26.7 (s), +79 (s, broad). 1H-NMR (C$_6$D$_6$, 300 MHz), some characteristic signals: 7.71 (s, 1H), 7.68 (s, 1H), 7.25 (s, 1H), 7.23 (s, 1H), 4.17 (s, 5H, cyclopentadiene ring), 3.31 (s, 3H, O—CH$_3$), 3.30 (s, 3H, O—CH$_3$), 3.27 (s, 3H, O—CH$_3$), 3.11 (s, 3H, O—CH$_3$), 2.14 (s, 3H, CH$_3$), 2.11 (s, 3H, CH$_3$).

b) Preparation of

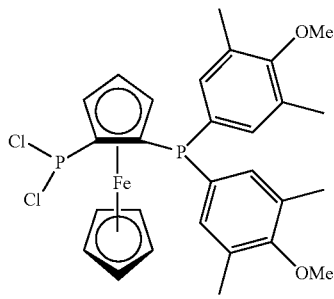

18.5 mmol of HCl (solution in diethyl ether) are slowly added dropwise to a solution of 2.34 g (3.08 mmol) of the compound a) in 20 ml of THF at 0° C. The cooling is then removed and the mixture is stirred for another 2 hours. The $^{31}$P-NMR (C$_6$D$_6$, 121 MHz) spectrum of a sample displays the following signals: 165 (PCl$_2$), 16 (broad, P(3,5-dimethyl-4-methoxyphenyl)$_2$-borane adduct. If the mixture is allowed to react for a shorter period, some free P(3,5-dimethyl-4-methoxyphenyl)$_2$ can also be seen in the region of −28 ppm.

c) Preparation of the Title Compound C3:

The dichlorophosphine obtained as described in step b) is reacted further without purification. After cooling to 0° C., 30 mmol of lithium aluminum hydride are slowly added a little at a time. After stirring at room temperature for 2 hours, the mixture is cooled back down to 0° C. and 10 ml of water are slowly added dropwise. Sodium sulfate is added to the resulting gray suspension. An organic phase separates out. This is separated off and the mixture is washed a number of times with heptane. The organic phases are combined and dried over sodium sulfate. After the solvent has been distilled off under reduced pressure, the crude product is dissolved in TBME and stirred in the presence of diethanolamine at 50° C. for a number of hours to remove borane. The TBME is subsequently washed with water, 1N HCl and again with water, dried over sodium sulfate and finally distilled off under reduced pressure. The desired product is obtained in good yield as a red oil and is used further without purification. $^{31}$P-NMR (C$_6$D$_6$, 121 MHz): −152 (d, PH$_2$), −22 (d, P(3,5-dimethyl-4-methoxyphenyl)$_2$). 1H-NMR (C$_6$D$_6$, 300 MHz), some characteristic signals: 7.52 (s, 1H), 7.49 (s, 1H), 7.19 (s, 1H), 7.16 (s, 1H), 4.04 (s, 5H, cyclopentadiene ring), 3.33 (s, 3H, O—CH$_3$), 3.27 (s, 3H, O—CH$_3$), 3.15 (s, 3H, O—CH$_3$), 2.88 (s, 3H, O—CH$_3$), 2.14 (s, 3H, CH$_3$), 2.08 (s, 3H, CH$_3$).

EXAMPLE C4

Preparation of

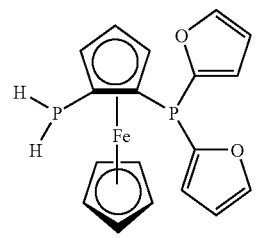

a) Preparation of 9.43 mmol of sec-butyllithium (1.3 molar in hexane) are added dropwise to a solution of 4 g (8.70 mmol) of the compound of example B1 in 60 ml of hexane/TBME 1:1 at −40° C. The reaction mixture is stirred further at this temperature for 2 hours. 9.43 mmol of difurylphosphine chloride are subsequently added to the resulting orange suspension. The reaction mixture is then allowed to warm slowly to room temperature while stirring. After stirring for 2 hours, the mixture is extracted with water/dichloromethane, the organic phases are dried over sodium sulfate and the solvent is distilled off under reduced pressure on a rotary evaporator. The solid crude product is purified by recrystallization from methanol. The product is obtained as a yellow crystalline material in a yield of 72%. $^{31}$P-NMR (C$_6$D$_6$, 121 MHz): −71.6 (s), +76.5 (s, broad). 1H-NMR (C$_6$D$_6$, 300 MHz), some characteristic signals: 7.20 (m, 1H), 6.81 (m, 1H), 6.52 (m, 1H), 5.97 (m, 2H), 5.21 (m, 1H), 4.27 (s, 5H, cyclopentadiene ring), 3.28 (s, 3H, O—CH$_3$), 3.13 (s, 3H, O—CH$_3$).

b) Preparation of

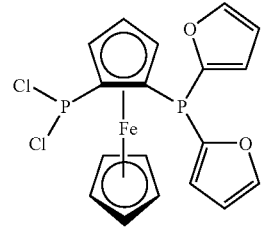

18.5 mmol of HCl (solution in diethyl ether) are added dropwise to a solution of 2.0 g (3.22 mmol) of the compound a) in 20 ml of THF at 0° C. over a period of 30 minutes. The cooling is then removed and the mixture is stirred for another 2 hours. A light-colored precipitate and a red oil are formed in the red solution. After the precipitate has been filtered off, the reaction mixture is measured by means of NMR. $^{31}$P-NMR (C$_6$D$_6$, 121 MHz): 162.7 (d), −72.5 (d).

c) Preparation of the Title Compound

The dichlorophosphine obtained as described in step b) is reacted further without purification. After cooling to 0° C., 32 mmol of lithium aluminum hydride are slowly added a little at a time. After stirring at room temperature for 3 hours, the mixture is cooled back down to 0° C. and 10 ml of water are slowly added dropwise. Sodium sulfate is added to the resulting gray suspension. An organic phase separates out. This is separated off and the mixture is washed a number of times with heptane. The organic phases are combined, washed with a little 0.5 molar aqueous methanesulfonic acid and subsequently with water, dried over sodium sulfate and the solvent is distilled off under reduced pressure. The desired product is obtained in good yield as an orange oil and is used further without purification. $^{31}$P-NMR (C$_6$D$_6$, 121 MHz): −67.5 (d, P(furyl)$_2$, −152.0 (d, PH$_2$). 1H-NMR (C$_6$D$_6$, 300 MHz), some characteristic signals: 7.27 (m), 6.73 (m), 6.51 (m), 6.07 (m), 5.97 (m), 3.94 (s, 5H, cyclopentadiene ring).

EXAMPLE C5

Preparation of

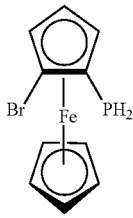

a) Preparation of

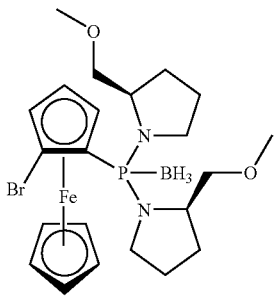

In a 50 ml round-bottom flask provided with an argon inlet, compound B2 (1.00 g, 2.18 mmol) is dissolved in dry TBME (5.00 ml) and n-hexane (5.00 ml) and the solution obtained is cooled to −30° C. This results in precipitation of the starting material as a yellow solid. s-Butyllithium (1.3 M in cyclohexane; 1.76 ml, 2.29 mmol, 1.05 equivalents) is added dropwise. During this addition, the yellow solid gradually goes into solution, the solution becomes orange-red and after about 30 minutes an orange solid precipitates.

After stirring at −30° C. for 2 hours, BrF$_2$C—CF$_2$Br (680 mg, 2.62 mmol, 1.2 equivalents) is added dropwise, the cooling bath is removed and the suspension is stirred for 2 hours while warming to RT. The reaction mixture is evaporated to dryness in a high vacuum on a rotary evaporator and used further in step b) without purification.$^{31}$P-NMR (C$_6$D$_6$, 121 MHz): 76.5 (m)

b) Preparation of

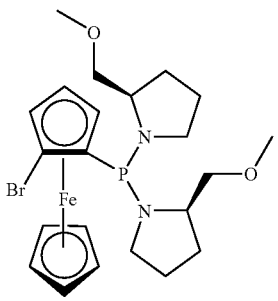

To remove the borane group, the residue obtained as described in a) is taken up in 5 ml of diethylamine and stirred overnight at 50° C. All volatile constituents are subsequently removed at 50° C. in an oil pump vacuum. The residue obtained is taken up three times in diethylamine (2.00 ml each time), stirred at 50° C. for 30 minutes and all volatile constituents are removed at 50° C. in an oil pump vacuum (30 minutes). The residue is taken up twice in dry TBME (2 ml) and all volatile constituents are removed at 50° C. in an oil pump vacuum. This leaves the product with the protection removed which is used further in step c) without purification.

c) Preparation of

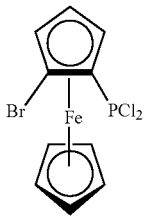

The reaction product as described in b) is dissolved in 5 ml of TBME and, at 0° C., 2.6 mmol of an HCl solution (2N in diethyl ether) is added dropwise while stirring. The reaction solution is subsequently separated off from the precipitated ammonium compounds by decantation and volatile constituents are removed under argon on a rotary evaporator. The residue is used directly in step d). $^{31}$P-NMR (C$_6$D$_6$, 121 MHz): 160.6 (s)

d) Preparation of the Title Compound 2 mmol of lithium aluminum hydride are suspended in 8 ml of absolute THF under argon and cooled to −78° C. The crude product prepared as described in c) is dissolved in 8 ml of absolute THF and added dropwise-to the cooled suspension of lithium aluminum hydride. The reaction mixture is stirred at this temperature for 30 minutes and then at 20° C. for 30 minutes. 1.7 ml of 2N NaOH are added dropwise to the suspension and the supernatant solution is filtered off and evaporated to isolate the orange title compound. The crude product is directly used further in example D1.

D) Preparation of 1-halo-2-phospholanylferrocenene

EXAMPLE D1

Preparation of

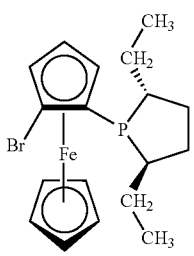

0.30 g (1 mmol) of the crude product from example C5d is dissolved in 5 ml of absolute THF, degassed and admixed with 1 ml (1 mmol) of a 1N solution of lithium diisopropylamide in THF. The resulting red solution is added dropwise to 0.22 g (1.20 mmol) of (3S,6S)-octane-3,6-diol sulfate. A further 1.2 ml of 1N lithium diisopropylamide in THF are added at room temperature and the mixture is stirred for another 60 minutes. 8 ml of water are added and the mixture is then extracted with diethyl ether. The organic phases are dried over sodium sulfate and evaporated. This gives the title compound as an orange, solid product.

E) Preparation of Ferrocene-diphosphines According to the Invention

EXAMPLE E1

Preparation of

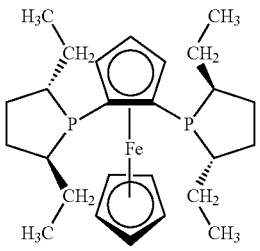

0.55 g (2.20 mmol) of the title compound C1 is dissolved in 10 ml of absolute THF, degassed and admixed with 2.2 ml (2.20 mmol) of a 1N solution of lithium diisopropylamide in THF. The red solution is added dropwise to 0.96 g (5.30 mmol) of (3R,6R)-octane-3,6-diol sulfate. A further 7 ml of 1N lithium diisopropylamide in THF are added at RT and the mixture is stirred for another 60 minutes. 20 ml of water are then added and the mixture is extracted with diethyl ether. The organic phases are dried over sodium sulfate and evaporated. This gives 0.848 g (82%) of the title compound. $^1$H NMR: 0.8-2.65 ppm (m, 32H); 4.20-4.25 (m, 6H); 4.37 (s, 1H); 4.40 (s, 1H) and $^{31}$P NMR: −11,0 (d), −3.3 (d).

EXAMPLE E2

Preparation of

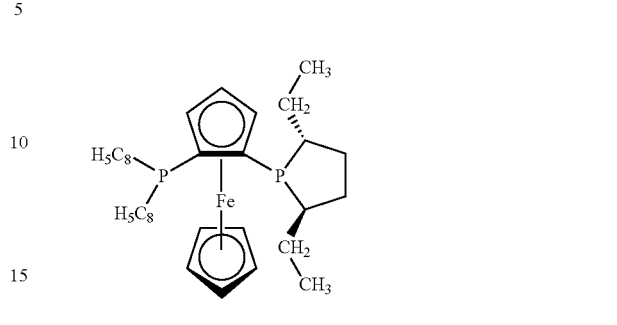

0.4 g (1 mmol) of the title compound of example C2 is dissolved in 5 ml of absolute THF, degassed and admixed with 1 ml (1 mmol) of a 1N solution of lithium diisopropylamide in THF. The red solution is added dropwise to 0.22 g (1.20 mmol) of (3S,6S)-octane-3,6-diol sulfate. A further 1.2 ml of 1N lithium diisopropylamide in THF are added dropwise at RT and the mixture is stirred for another 60 minutes. 8 ml of water are added and the mixture is then extracted with diethyl ether. The organic phases are dried over sodium sulfate and evaporated. This gives the title compound as an orange solid.

EXAMPLE E3

Preparation of

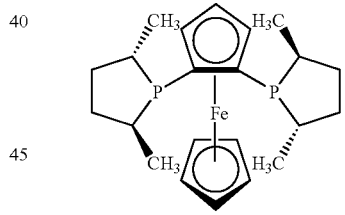

0.7 g (3.80 mmol) of the title compound C1 is dissolved in 10 ml of absolute THF, degassed and admixed with 1.05 molar equivalents of a 1N solution of lithium diisopropylamide in THF. The red solution is added dropwise to 1.21 g (6.72 mmol) of (2R,5R)-hexane-2,5-diol sulfate. A further 3.4 molar equivalents of 1N lithium diisopropylamide in THF are added at room temperature and the mixture is stirred for another 60 minutes. 20 ml of water are then added and the mixture is extracted with diethyl ether. The organic phases are dried over sodium sulfate and evaporated. This gives 0.60 g (52%) of the title compound. 1H NMR: 0.8-0.9 (dd, 3H), 1.1-1.2 (m, 2H), 1.2-1.3 (dd, 3H), 1.4-1.5 (dd, 3H), 1.5-1.6 (dd, 3H), 1.8-2.2 (m, 5H), 2.3-2.4 (m, 1H), 2.6-2.7 (m, 1H), 3.1-3.2 (m, 1H), 4.0 (m, 1H), 4.2 (m, 6H), 4.3 (m, 1H) and $^{31}$P NMR: −8.3 (d), 5.9 (d).

EXAMPLE E4

Preparation of

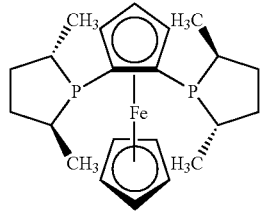

6.72 g (26.88 mmol) of the title compound C1 are dissolved in 100 ml of absolute THF, degassed and admixed with 1.05 molar equivalents of a 1N solution of lithium diisopropylamide in THF. The red solution is added dropwise to 10.17 g (56.45 mmol) of (2R,5R)-hexane-2,5-diol ditosylate. A further 3.4 molar equivalents of 1N lithium diisopropylamide in THF are added at room temperature and the mixture is stirred for another 60 minutes. 20 ml of water are then added and the mixture is extracted with diethyl ether. The organic phases are dried over sodium sulfate, evaporated and purified by means of column chromatography (pentane:diethyl ether, 4:1). This gives 4.47 g (40%) of the title compound. The NMR spectra correspond to those of the compound of example E3.

EXAMPLE E5

Preparation of

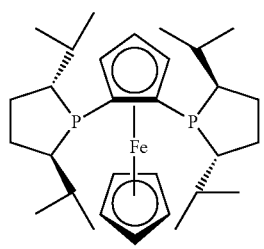

0.6 g (2.40 mmol) of the title compound C1 is dissolved in 10 ml of absolute THF, degassed and admixed with 1.05 molar equivalents of a 1N solution of lithium diisopropylamide in THF. The red solution is added dropwise to 1.36 g (5.76 mmol) of (3S,6S)-2,7-dimethyloctane-2,5-diol sulfate. A further 3.4 molar equivalents of 1N lithium diisopropylamide in THF are added at room temperature and the mixture is stirred for another 60 minutes. 20 ml of water are then added and the mixture is extracted with diethyl ether. The organic phases are dried over sodium sulfate, evaporated and purified by means of column chromatography (pentane:diethyl ether, 4:1). This gives 0.85 g (67%) of the title compound. 31P NMR: −21.8 (d), −0.1 (d).

EXAMPLE E6

Preparation of

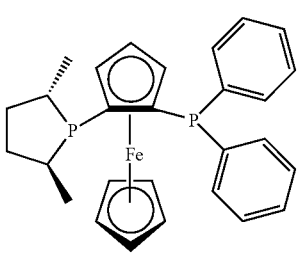

1.05 molar equivalents of a 1N solution of lithium diisopropylamide in THF are added to a solution of 410 mg (1.02 mmol) of the title compound C2' in 12 ml of THF. The solution is added dropwise to 221 mg (1.22 mmol) of (2R,5R)-hexane-2,5-diol sulfate. A further 1.2 molar equivalents of a 1N solution of lithium diisopropylamide in THF are added dropwise at RT and the mixture is stirred for another one hour. After the solvent has been distilled off, the crude product is purified by column chromatography (silica gel 60, eluent: ethyl acetate). The product is isolated in a yield of 45%. $^{31}$P-NMR (C$_6$D$_6$, 121 MHz): −6.0 (d, J$_{PP}$~90 Hz), −24.2 (d, J$_{PP}$~90 Hz).

EXAMPLE E7

Preparation of

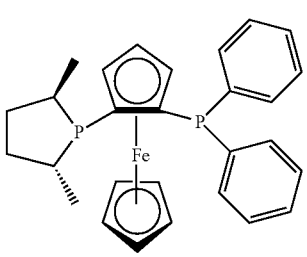

1.05 molar equivalents of a 1N solution of lithium diisopropylamide in THF are added to a solution of 436 mg (1.09 mmol) of the compound C2' in 12 ml of THF. The solution is added dropwise to 235 mg (1.3 mmol) of (2S,5S)-hexane-2,5-diol sulfate. A further 1.2 molar equivalents of a 1N solution of lithium diisopropylamide in THF are added dropwise at room temperature and the mixture is stirred for another 1 hour. After the solvent has been distilled off, the crude product is purified by means of column chromatography (silica gel 60, eluent: ethyl acetate). The product is isolated in a yield of 40%. $^{31}$P-NMR (C$_6$D$_6$, 121 MHz): −3.2 (d, J$_{PP}$~50 Hz), −23.1 (d, J$_{PP}$~50 Hz).

EXAMPLE E8

Preparation of

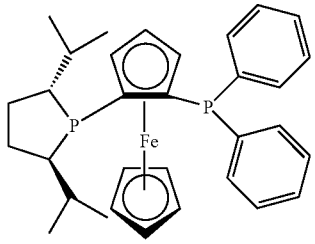

1.05 molar equivalents of a 1N solution of lithium diisopropylamide in THF are added to a solution of 450 mg (1.12 mmol) of the compound C2' in 10 ml of THF. The solution is added dropwise to 295 mg (1.34 mmol) of (3S,6S)-2,7-dimethyloctane-2,5-diol sulfate. A further 1.2 molar equivalents of a 1N solution of lithium diisopropylamide in THF are added dropwise at RT and the mixture is stirred for another 1 hour. After the solvent has been distilled off, the crude product is purified by column chromatography (silica gel 60, eluent: ethyl acetate). The product is isolated in a yield of 50%. $^{31}$P-NMR (C$_6$D$_6$, 121 MHz): −13.0 (d, J$_{PP}$~80 Hz), −24.7 (d, J$_{PP}$~80 Hz).

EXAMPLE E9

Preparation of

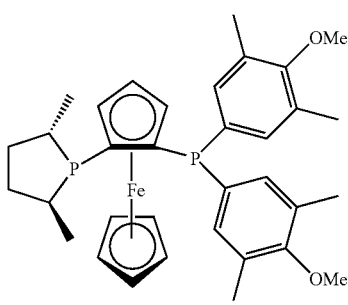

1.05 molar equivalents of a 1N solution of lithium diisopropylamide in THF are added to a solution of 1.13 g (3.08 mmol) of the compound C3 in 20 ml of THF. The solution is added dropwise to 3.7 mmol of (2R,5R)-hexane-2,5-diol sulfate. A further 1.2 molar equivalents of a 1N solution of lithium diisopropylamide in THF are added dropwise at room temperature (RT) and the mixture is stirred for another 1 hour. After the solvent has been distilled off, the crude product is extracted in ethyl acetate/10% aqueous NaBF$_4$. The organic phases are dried over sodium sulfate and evaporated under reduced pressure. The orange product is obtained in a yield of 80%. If necessary, it can be purified by column chromatography (silica gel 60, eluent: heptane/TBME 3:1). $^{31}$P-NMR (C$_6$D$_6$, 121 MHz): −6.6 (d, J$_{PP}$~85 Hz), −25.5 (d, J$_{PP}$~85 Hz).

EXAMPLE E10

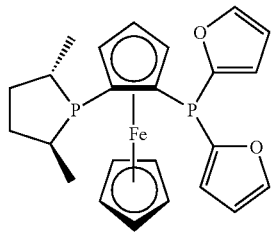

Preparation of 1.05 molar equivalents of a 1N solution of lithium diisopropylamide in THF are added to a solution of 400 mg (1.05 mmol) of the compound C4 in 10 ml of THF. The solution is added dropwise to 1.26 mmol of (2R,5R)-hexane-2,5-diol sulfate. A further 1.2 molar equivalents of a 1N solution of lithium diisopropylamide in THF are added dropwise at RT and the mixture is then stirred for another one hour. After the solvent has been distilled off, the crude product is extracted in ethyl acetate/10% aqueous NaBF$_4$. The organic phases are dried over sodium sulfate and evaporated under reduced pressure. The orange product is obtained in a yield of 76%. If necessary, it can be purified by column chromatography (silica gel 60, eluent: heptane/TBME 3:1). $^{31}$P-NMR (C$_6$D$_6$, 121 MHz): −6.8 (d, J$_{PP}$~100 Hz), −71.1 (d, J$_{PP}$~100 Hz).

EXAMPLE E11

Preparation of a Phosphonium Salt, viz. 1,2-bis(2,5-dimethylphospholano)-ferrocenyl bis(hexafluorophosphate)

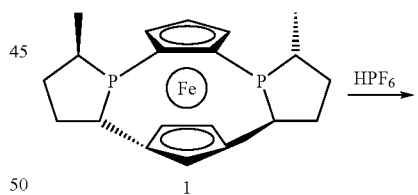

1

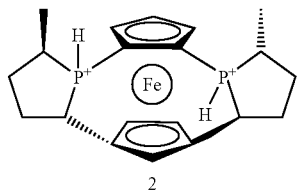

2

192 mg (0.46 mmol) of 1 are dissolved in 2 ml of dichloromethane and admixed at 0° C. with 135 μl (0.92 mmol) of HPF$_6$ (65% in water). The mixture is evaporated. Treatment with 5 ml of diethyl ether gives a yellow solid (327 mg, 86%). $^{31}$P NMR (ppm): −143 (septet, PF$_6$), −8 (broad s, P$^+$)

F) Preparation of Metal Complexes

EXAMPLE F1

Preparation of a Rhodium Complex 1 equivalent of a suspension of [Rh(COD)$_2$]BF$_4$ in 5 times its weight of THF is heated to 65° C. while stirring. A solution of 1 equivalent of the diphosphine of example E1 in 5 times its weight of THF is subsequently added dropwise over a period of 20 minutes. 4 ml of TBME are then added dropwise to the reaction solution. Slow cooling overnight results in formation of crystals which are isolated by filtration and washing with THF. The mother liquor is completely evaporated under reduced pressure, the residue is taken up in TBME and rubbed with a glass rod in an ultrasonic bath. This results in formation of fine yellow crystals. The suspension is cooled to 0° C., allowed to stand for 3 hours and filtered. After washing with TBME, these crystals are collected and dried in a high vacuum. Both crystal fractions have identical NMR spectra. $^{31}$P NMR (CDCl$_3$, 121 MHz): 58.6 (d), 46.1 (d).

EXAMPLE F2

Preparation of

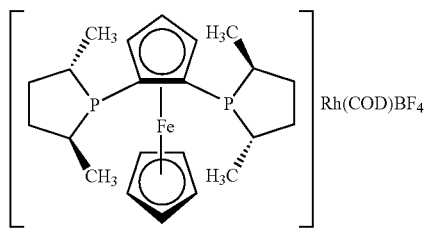

Using the general method in example F1, the compound from example E4 is reacted with [Rh(COD)$_2$]BF$_4$ to give the title compound in a yield of 90%. $^{31}$P NMR: 48.7 (dd), 60.0 (d).

EXAMPLE F3

Preparation of

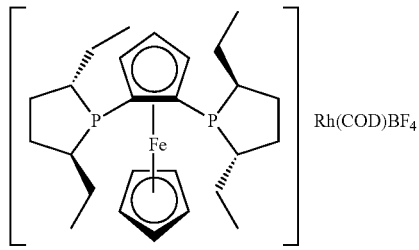

Using the general method in example F1, the compound from example E1 is reacted with [Rh(COD)$_2$]BF$_4$ to give the title compound in a yield of 87%. $^{31}$P NMR: 46.5 (dd), 58.4 (dd).

EXAMPLE F4

Preparation of

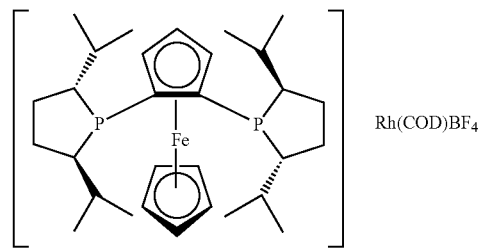

Using the general method in example F1, the compound from example E5 is reacted with [Rh(COD)$_2$]BF$_4$ to give the title compound in a yield of 67%. $^{31}$P NMR: 46.5 (dd), 58.3 (d).

EXAMPLE F5

Preparation of

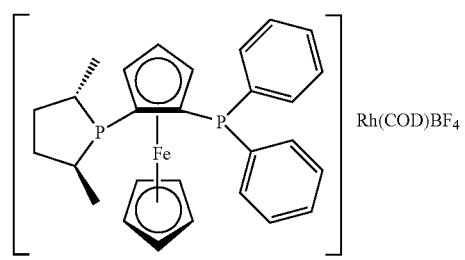

Using the general method in example F1, the compound from example E6 is reacted with [Rh(COD)$_2$]BF$_4$ to give the title compound in a yield of 70%. $^{31}$P-NMR (C$_6$D$_6$, 121 MHz): 53.5 (m), 40.0 (m).

EXAMPLE F6

Preparation of

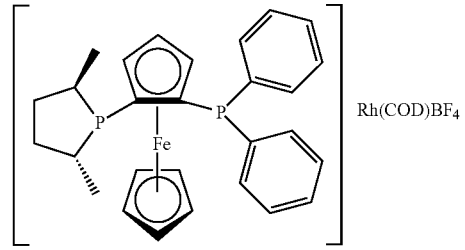

Using the general method in example F1, the compound from example E7 is reacted with [Rh(COD)$_2$]BF$_4$ to give the title compound in a yield of 85%. $^{31}$P-NMR (C$_6$D$_6$, 121 MHz): 59.8 (m), 37.1 (m).

EXAMPLE F7

Preparation of

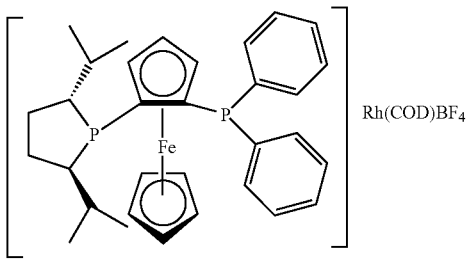

Using the general method in example F1, the compound from example E8 is reacted with [Rh(COD)$_2$]BF$_4$ to give the title compound in a yield of 55%. $^{31}$P-NMR (C$_6$D$_6$, 121 MHz): 42.0 (m), 39.4 (m).

EXAMPLE F8

Preparation of

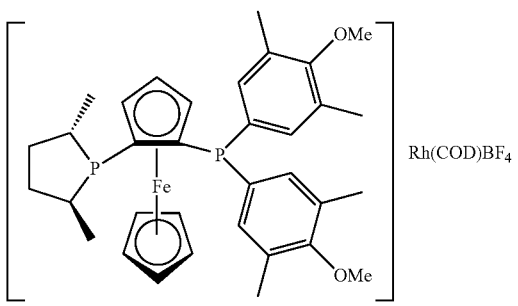

Using the general method in example F1, the compound from example E9 is reacted with [Rh(COD)$_2$]BF$_4$ to give the title compound in a yield of 35%. $^{31}$P-NMR (C$_6$D$_6$, 121 MHz): 52.2 (m), 37.0 (m).

EXAMPLE F9

Preparation of

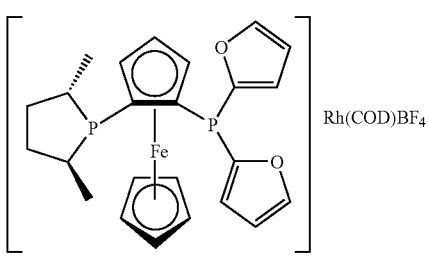

Using the general method in example F1, the compound from example E10 is reacted with [Rh(COD)$_2$]BF$_4$ to give the title compound in a yield of 62%. $^{31}$P-NMR (C$_6$D$_6$, 121 MHz): 53.4 (m), 1.0 (m).

G) USE EXAMPLES

In the use examples, both conversion and the optical yields (enantiomeric excess ee) have not been optimized.

EXAMPLE G1

Hydrogenation of Dimethyl Itaconate
(Hydrogenation Using an Isolated Rh Complex)

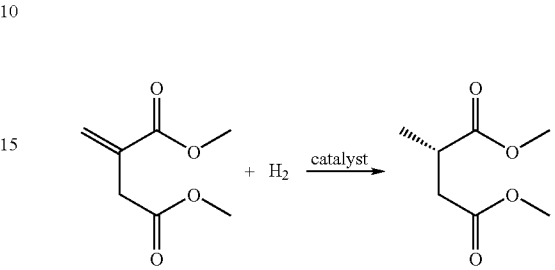

3.85 mg (0.005 mmol) of the rhodium complex of example F1 are placed in a 25 ml flask provided with a magnetic stirrer and gas and vacuum connections. The flask is closed by means of a septum and filled with argon by multiple evacuation and admission of argon. A degassed solution of 158 mg (1 mmol) of dimethyl itaconate in 4 ml of methanol is added through the septum by means of a syringe provided with a needle and the mixture is stirred for 10 minutes. The stirrer is switched off, the flask is filled with argon by application of a vacuum and admission of hydrogen (atmospheric pressure) and the hydrogen inlet is left open. The hydrogenation is started by switching on the stirrer. After one hour, the stirrer is switched off and the reaction solution is analyzed on a gas chromatograph provided with a chiral column (Chirasil-L-val). The conversion is quantitative, and the optical yield ee of the hydrogenation product (dimethyl methylsuccinate) is greater than 99%.

EXAMPLE G2

Hydrogenation of Dimethyl Itaconate

The hydrogenation is carried out by a method similar to example G2 using the rhodium complex of example F5. The conversion is quantitative, and the optical yield ee of the hydrogenation product (dimethyl methylsuccinate) is greater than 98%.

EXAMPLE G3

Hydrogenation of Dimethyl Itaconate
(Hydrogenation Using Catalyst Prepared in situ)

(0.0055 mmol) of the ligand of example E9 are placed in a 25 ml flask provided with a magnetic stirrer and gas and vacuum connections. The flask is closed by means of a septum and filled with argon by multiple evacuation and admission of argon. A degassed solution of 0.005 mmol of [Rh(COD)]BF$_4$ in 1 ml of methanol is introduced through the septum by means of a syringe provided with a needle, the solution is stirred for 5 minutes and a solution of 158 mg (1 mmol) of dimethyl itaconate in 4 ml of methanol is subsequently added and the mixture is stirred for 10 minutes. The stirrer is switched off, the flask is filled with hydrogen by application of a vacuum and admission of hydrogen (atmospheric pressure) and the hydrogen inlet is left open. The hydrogenation is started by switching on the stirrer. After one hour, the stirrer is switched off and the reaction solution is analyzed on a gas chromatograph provided with a chiral column (Chirasil-L-val). The conversion is quantitative, and the optical yield ee of the hydrogenation product (dimethyl methylsuccinate) is greater than 97%.

EXAMPLE G4

Hydrogenation of

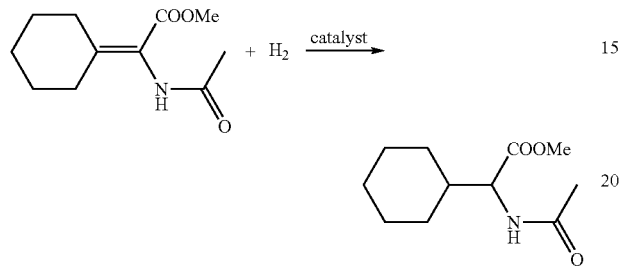

(0.011 mmol) of the ligand of example E4 are placed in a 25 ml flask provided with a magnetic stirrer and gas and vacuum connections. The flask is closed by means of a septum and filled with argon by multiple evacuation and admission of argon. A degassed solution of 0.01 mmol [Rh(norbornadiene)$_2$]BF$_4$ in 1 ml of methanol is introduced through the septum by means of a syringe provided with a needle, the solution is stirred for 5 minutes and a solution of 1 mmol of N-acetylcyclohexylideneglycine methyl ester in 4 ml of methanol is subsequently added and the mixture is stirred for 10 minutes. The stirrer is switched off, the flask is filled with hydrogen by application of a vacuum and admission of hydrogen (atmospheric pressure) and the hydrogen inlet is left open. The hydrogenation is started by switching on the stirrer. After stirring overnight, the stirrer is switched off and the reaction solution is analyzed on a gas chromatograph provided with a chiral column (Chirasil-L-val). The conversion is above 80% and the optical yield ee of N-acetylcyclohexylglycine methyl ester is 91%.

EXAMPLE G5

Hydrogenation of

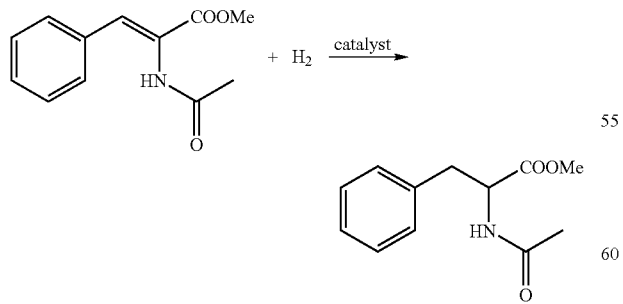

The hydrogenation is carried out by a method similar to example G4 using methyl acetamidocinnamate E5. According to gas chromatography (Chirasil-L-val), the conversion is quantitative and the optical yield ee is 97%.

EXAMPLE G6

Hydrogenation of

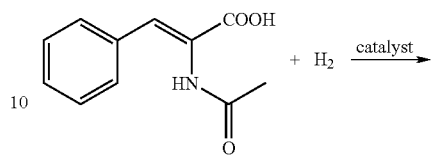

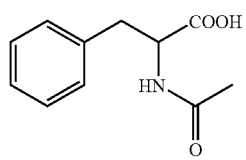

The hydrogenation is carried out by a method similar to example G4 using acetamidocinnamic acid. The product is converted into the corresponding methyl ester by means of diazomethane and is analyzed by gas chromatography (Chirasil-L-val). The conversion is quantitative and the optical yield ee is 97%.

The invention claimed is:

1. A compound of the formula I in the form of a racemate, a mixture of diastereomers or an essentially pure diastereomer,

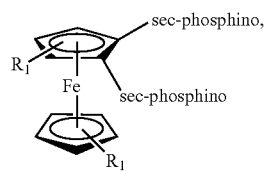

(I)

where
R$_1$ is a hydrogen atom or C$_1$-C$_4$-alkyl and at least one sec-phosphine group is an unsubstituted or substituted cyclic phosphino group, or a phosphonium salt thereof having one or two monovalent anions or one divalent anion.

2. The compound as claimed in claim 1, wherein the cyclic sec-phosphino corresponds to the formula II, IIa, IIb or IIc,

(II)

(IIa)

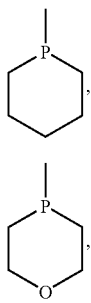 (IIb)

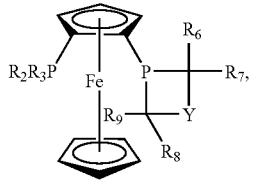 (IIc)

which are unsubstituted or substituted by one or more —OH, $C_1$-$C_8$-alkyl, $C_4$-$C_8$-cycloalkyl, $C_1$-$C_6$-alkoxy, $C_1$-$C_4$-alkoxy-$C_1$-$C_4$-alkyl, phenyl, $C_1$-$C_4$-alkyl- or $C_1$-$C_4$-alkoxyphenyl, benzyl, $C_1$-$C_4$-alkyl- or $C_1$-$C_4$-alkoxybenzyl, benzyloxy, $C_1$-$C_4$-alkyl- or $C_1$-$C_4$-alkoxybenzyloxy or $C_1$-$C_4$-alkylidenedioxyl groups.

3. The compound as claimed in claim 2, wherein substituents are present in one or both α positions relative to the P atom.

4. The compound as claimed in claim 1, wherein the compound of the formula I corresponds to the formula III or IV,

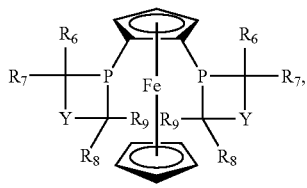 (III)

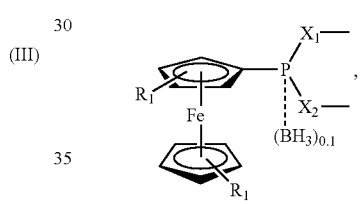 (IV)

where
R$_2$ and R$_3$ are each, independently of one another, a hydrocarbon radical which has from 1 to 20 carbon atoms and is unsubstituted or substituted by halogen, $C_1$-$C_6$-alkyl, $C_1$-$C_6$-haloalkyl, $C_1$-$C_6$-alkoxy, $C_1$-$C_6$-haloalkoxy, di-$C_1$-$C_4$-alkylamino, $(C_6H_5)_3$Si, $(C_1$-$C_{12}$-alkyl)$_3$Si, or —CO$_2$—$C_1$-$C_6$-alkyl, Y is —CH$_2$—, —CH$_2$CH$_2$—, —CH$_2$CH$_2$CH$_2$—, —CH(OH)CH(OH)—, —CH(OC$_1$-$C_4$-alkyl)CH(OC$_1$-$C_4$-alkyl)- or a radical of the formula

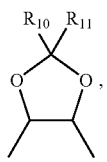

R$_6$, R$_7$, R$_8$ and R$_9$ are each, independently of one another, H, $C_1$-$C_4$-alkyl or benzyl, and at least one of the radicals R$_6$, R$_7$, R$_8$ and R$_9$ is $C_1$-$C_4$-alkyl, benzyl or —CH$_2$—O—$C_1$-$C_4$-alkyl or —CH$_2$—O—$C_6$-$C_{10}$-aryl, R$_{10}$ is H or $C_1$-$C_4$-alkyl and R$_{11}$ is $C_1$-$C_4$-alkyl.

5. A process for preparing compounds of the formula I in the form of racemates, mixtures of diastereomers or essentially pure diastereomers,

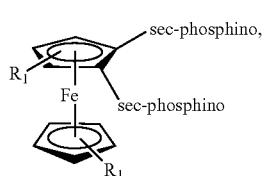 (I)

where
R$_1$ is a hydrogen atom or $C_1$-$C_4$-alkyl and at least one sec-phosphino is an unsubstituted or substituted cyclic phosphino group, which comprises the steps a) reaction of a compound of the formula V

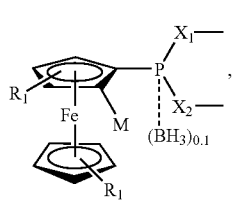 (V)

where
(BH$_3$)$_{0.1}$ means that the group BH$_3$ may be present or not be present, X$_1$ and X$_2$ are each, independently of one another, O or N and C-bonded hydrocarbon or heterohydrocarbon radicals are bound to the free bonds of the O and N atoms, with at least equivalent amounts of a lithium alkyl, a magnesium Grignard compound or an aliphatic Li sec-amide or X$_3$Mg sec-amide to form a compound of the formula VI, (VI)

where
M is —Li or —MgX$_3$ and X$_3$ is Cl, Br or I, b) reaction of the compound of the formula VI with at least equivalent amounts of a di-sec-aminophosphine halide, a dialkoxyphosphine halide, di-sec-amino-P(O) halide, dialkoxy-P(O) halide or PCl$_3$ or PBr$_3$ to form a compound of the formula VII

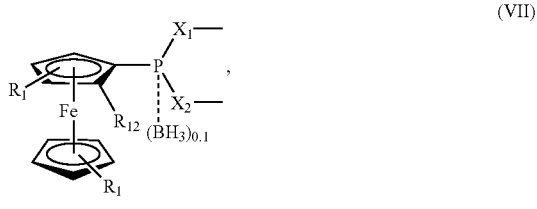

(VII)

where

R$_{12}$ is —PCl$_2$, —PBr$_2$, di(sec-amino)P—, dialkoxyP—, di-sec-amino-P(O)—, dialkoxy-P(O)—, and b1) removing any borane group present from a compound of the formula VII, then splitting off the radicals (hetero)hydrocarbon-X$_1$, (hetero)hydrocarbon-X$_2$ or X$_1$-(hetero)hydrocarbon-X$_2$ or di-sec-amino or dialkoxy by means of HCl or HBr to form a —PCl$_2$ group or —PBr$_2$ group and then hydrogenating the —(O)PCl$_2$ groups, —(O)PBr$_2$ groups, —PCl$_2$ groups or —PBr$_2$ groups to form a compound of the formula VIII or b2) splitting off the radicals (hetero)hydrocarbon-X$_1$, (hetero)hydrocarbon-X$_2$ or X$_1$-(hetero)hydrocarbon-X$_2$ or di-sec-amino or dialkoxy from a compound of the formula VII by means of HCl or HBr to form a —PCl$_2$ group or —PBr$_2$ group and then hydrogenating the —(O)PCl$_2$ groups, —(O)PBr$_2$ groups, —PCl$_2$ groups or —PBr$_2$ groups and then removing the borane group to form a compound of the formula VIII,

(VIII)

or c) reaction of a compound of the formula VI with a sec-phosphine halide to form a compound of the formula IX,

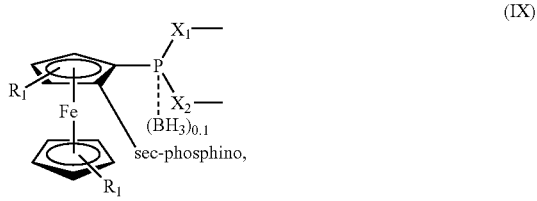

(IX)

c1) removing any borane group present from a compound of the formula IX, then splitting off the radicals (hetero)hydrocarbon-X1, (hetero)hydrocarbon-X$_2$ or X$_1$-(hetero)hydrocarbon-X$_2$ by means of HCl or HBr to form a —PCl$_2$ group or —PBr$_2$ group and then hydrogenating the —PCl$_2$ groups or —PBr$_2$ groups to form a compound of the formula X or c2) splitting off the radicals (hetero)hydrocarbon-X$_1$, (hetero)hydrocarbon-X$_2$ or X$_1$-(hetero)-hydrocarbon-X$_2$ from a compound of the formula IX by means of HCl or HBr to form a —PCl$_2$ group or —PBr$_2$ group and then hydrogenating the —PCl$_2$ groups or —PBr$_2$ groups and then removing the borane group to form a compound of the formula X

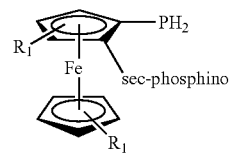

(X)

or d) reaction of a compound of the formula VI with a halogenating reagent to form a compound of the formula XI

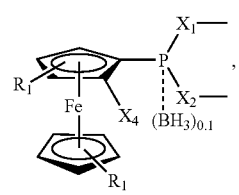

(X)

where X$_4$ is Cl, Br or I, d1) removing any borane group present from a compound of the formula XI, then splitting off the radicals (hetero)hydrocarbon-X$_1$, (hetero)hydrocarbon-X$_2$ or X$_1$-(hetero)hydrocarbon-X$_2$ by means of HCl or HBr to form a —PCl$_2$ group or —PBr$_2$ group and then hydrogenating the —PCl$_2$ group or —PBr$_2$ group to form a compound of the formula XII or d2) splitting off the radicals (hetero)hydrocarbon-X$_1$, (hetero)hydrocarbon-X$_2$ or X$_1$-(hetero)-hydrocarbon-X$_2$ from a compound of the formula XI by means of HCl or HBr to form a —PCl$_2$ group or —PBr$_2$ group and then hydrogenating the —PCl$_2$ groups or —PBr$_2$ groups and then removing the borane group to form a compound of the formula XII

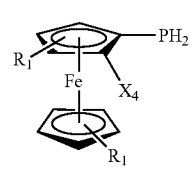

(XII)

and d3) reacting the compound of the formula XII with a metalated sec-phosphide to form a compound of the formula X, e) reaction of the compound of the formula VII with at least 2 equivalents and of the compound of the formula X with at least 1 equivalent of a cyclic sulfate or an open-chain disulfonate to produce compounds of the formula I in which one or both sec-phosphino groups are cyclic sec-phosphino or f) reaction of a compound of the formula XII with at least 1 equivalent of a cyclic sulfate or an open-chain disulfonate to produce compounds of the formula XIII,

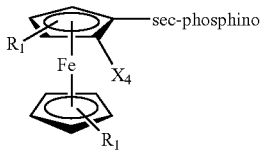

(XIII)

where sec-phosphino is cyclic sec-phosphino which may, if appropriate, be protected by $BH_3$, and then reaction of a compound of the formula XIII with at least 1 equivalent of a lithium alkyl and then with at least 1 equivalent of a sec-phosphine halide to form a compound of the formula I.

6. A compound of the formula VII, IX or XI,

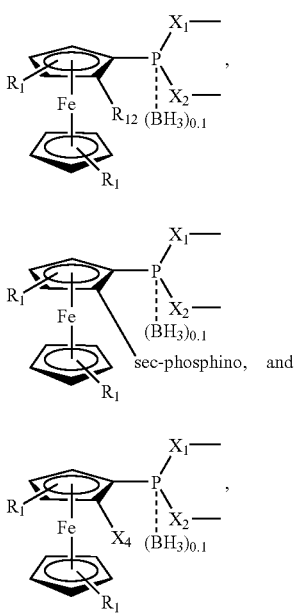

(VII)

(IX)

(XI)

where
(BH$_3$)$_{0.1}$ means that the group $BH_3$ may be present or not be present, sec-phosphino is an unsubstituted or substituted cyclic phosphino group,
$X_1$ and $X_2$ are each, independently of one another, O or N and C-bonded hydrocarbon or heterohydrocarbon radicals are bound to the free bonds of the O and N atoms and
$R_1$, $R_{12}$ and $X_4$ are as defined in claim 5.

7. A compound of the formula VIII, X or XII,

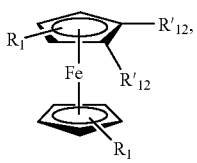

(VIII)

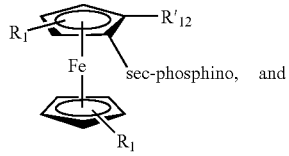

(X)

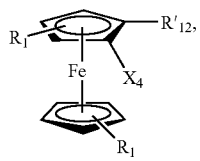

(XII)

where
sec-phosphino is an unsubstituted or substituted cyclic phosphino group,
$R'_{12}$ is —PCl$_2$, —PBr$_2$ or —PH$_2$ and $R_1$ and $X_4$ are as defined in claim 5.

8. A compound of the formula XIII

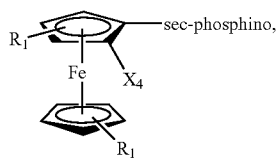

(XIII)

where $R_1$ and $X_4$ are as defined in claim 5 and sec-phosphino is cyclic sec-phosphino.

9. A complex of a metal selected from the group consisting of transition metals Cu, Ag, Au, Ni, Co, Rh, Pd, Ir, Ru and Pt with a compound of the formula I according to claim 1 as ligand.

10. The metal complex as claimed in claim 9, wherein the transition metal is ruthenium, rhodium or iridium.

11. The metal complex as claimed in claim 9, which corresponds to the formula XIV or XV, $$A_1 MeL_n \quad (XIV),$$

$$(A_1 MeL_n)^{(z+)}(E^-)_z \quad (XV),$$

where $A_1$ is a compound of the formula I,
L represents identical or different monodentate, anionic or nonionic ligands, or $L_2$ represents identical or different bidentate, anionic or nonionic ligands;
n is 2, 3 or 4 when L is a monodentate ligand or n is 1 or 2 when L is a bidentate ligand;
z is 1, 2 or 3;
Me is a metal selected from the group consisting of Rh, Ir and Ru; with the metal having the oxidation state 0, 1, 2, 3 or 4;
$E^-$ is the anion of an oxo acid or complex acid; and
the anionic ligands balance the charge of the oxidation state 1, 2, 3 or 4 of the metal.

12. The metal complex as claimed in claim 9, which corresponds to the formula XII or XIV, $$[A_1 Me_2 YZ] \quad (XVI),$$

$$[A_1 Me_2 Y]^+ E_1^- \quad (XVII),$$

where
- $A_1$ is a compound of the formula I;
- $Me_2$ is rhodium or iridium;
- Y represents two olefins or diene;
- Z is Cl, Br or I; and
- $E_1^-$ is the anion of an oxo acid or complex acid.

13. A process for preparing chiral organic compounds by asymmetric addition of hydrogen, boron hydrides or silanes onto a carbon-carbon or carbon-heteroatom multiple bond in prochiral organic compounds or asymmetric addition of carbon nucleophiles or amines onto allyl compounds in the presence of a catalyst, wherein the addition reaction is carried out in the presence of catalytic amounts of at least one metal complex as claimed in claim 9.

14. A method for preparing chiral organic compounds comprising asymmetrically adding hydrogen, boron hydrides or silanes onto a carbon-carbon or carbon-heteroatom multiple bond in prochiral organic compounds, or asymmetrically adding carbon nucleophiles or amines onto allyl compounds, in the presence of a homogeneous catalyst, wherein the homogeneous catalyst is a complex to claim 9.

* * * * *